(12) United States Patent
McCall et al.

(10) Patent No.: US 11,382,922 B2
(45) Date of Patent: Jul. 12, 2022

(54) AQUEOUS ORAL PHARMACEUTICAL SUSPENSION COMPOSITIONS

(71) Applicant: ReveraGen BioPharma, Inc., Rockville, MD (US)

(72) Inventors: John McCall, Boca Grande, FL (US); Jesse Damsker, Alexandria, VA (US)

(73) Assignee: ReveraGen BioPharma, Inc., Rockville, MD (US)

( * ) Notice: Subject to any disclaimer, the term of this patent is extended or adjusted under 35 U.S.C. 154(b) by 132 days.

(21) Appl. No.: 16/811,973

(22) Filed: Mar. 6, 2020

(65) Prior Publication Data
US 2020/0281942 A1 Sep. 10, 2020

Related U.S. Application Data

(60) Provisional application No. 62/815,097, filed on Mar. 7, 2019.

(51) Int. Cl.
| | |
|---|---|
| *A61K 31/573* | (2006.01) |
| *A61K 9/00* | (2006.01) |
| *A61K 47/10* | (2017.01) |
| *A61K 47/36* | (2006.01) |
| *A61K 9/08* | (2006.01) |

(52) U.S. Cl.
CPC .......... *A61K 31/573* (2013.01); *A61K 9/0053* (2013.01); *A61K 9/08* (2013.01); *A61K 47/10* (2013.01); *A61K 47/36* (2013.01)

(58) Field of Classification Search
CPC ...... A61K 31/573; A61K 9/0053; A61K 9/08; A61K 47/10; A61K 47/36
See application file for complete search history.

(56) References Cited

U.S. PATENT DOCUMENTS

| | | | |
|---|---|---|---|
| 2,776,927 A | 1/1957 | Shull |
| 2,838,536 A | 6/1958 | Magerklein |
| 2,894,963 A | 7/1959 | Gould |
| 2,957,893 A | 10/1960 | Herzog |
| 2,980,713 A | 4/1961 | Chemerda |
| 3,004,965 A | 10/1961 | Kerwin |
| 3,009,933 A | 11/1961 | Robinson |
| 3,047,468 A | 7/1962 | Origoni |
| 3,053,866 A | 9/1962 | Chemerda |
| 3,087,938 A | 4/1963 | Reimann |
| 3,098,086 A | 7/1963 | Wettstein |
| 3,127,425 A | 3/1964 | Reimann |
| 3,284,477 A | 11/1966 | Rausser |
| 3,463,852 A | 8/1969 | Reimann |

(Continued)

FOREIGN PATENT DOCUMENTS

| | | |
|---|---|---|
| CA | 975755 A | 10/1975 |
| CA | 983919 A | 2/1976 |

(Continued)

OTHER PUBLICATIONS

Lindner, V., "The NF-kappaB and IkappaB System in Injured Arteries", Pathobiol., 66(6):311-20, (1998).

(Continued)

*Primary Examiner* — San Ming R Hui
(74) *Attorney, Agent, or Firm* — Dennis A. Bennett; Lauren L. Stevens; C A Schlecht

(57) ABSTRACT

Provided is an aqueous oral pharmaceutical suspension composition comprising vamorolone Form I. Also provided are methods for its preparation and its use.

26 Claims, 5 Drawing Sheets

(56) References Cited

U.S. PATENT DOCUMENTS

| | | |
|---|---|---|
| 3,681,405 A | 8/1972 | Laurent |
| 3,842,105 A | 10/1974 | Hofmeister |
| 3,891,631 A | 6/1975 | Phillipps |
| 3,923,985 A | 12/1975 | Marechal |
| 4,041,055 A | 8/1977 | Shephard |
| 4,076,708 A | 2/1978 | Green |
| 4,260,464 A | 4/1981 | Kerb |
| 4,318,853 A | 3/1982 | Ayer |
| 4,336,200 A | 6/1982 | Ayer |
| 4,404,141 A | 9/1983 | Annen |
| 4,427,591 A | 1/1984 | Ayer |
| 4,444,689 A | 4/1984 | Ayer |
| 4,472,393 A | 9/1984 | Shapiro |
| 4,555,507 A | 11/1985 | Annen |
| 4,613,463 A | 9/1986 | Sacks |
| 4,645,763 A | 2/1987 | Annen |
| 4,701,451 A | 10/1987 | Annen |
| 4,771,042 A | 9/1988 | Braughler |
| 4,777,165 A | 10/1988 | Annen |
| 4,876,250 A | 10/1989 | Clark |
| 4,891,426 A | 1/1990 | Vanrheenen |
| 4,910,192 A | 3/1990 | Avery |
| 4,920,216 A | 4/1990 | Breslow |
| 4,929,395 A | 5/1990 | Vanrheenen |
| 4,948,533 A | 8/1990 | Braughler |
| 4,975,536 A | 12/1990 | Shephard |
| 4,975,537 A | 12/1990 | Aristoff |
| 4,977,255 A | 12/1990 | Livingston |
| 4,990,612 A | 2/1991 | Vanrheenen |
| 4,994,443 A | 2/1991 | Folkman |
| 5,001,116 A | 3/1991 | Folkman |
| 5,225,335 A | 7/1993 | Kominek |
| 5,248,773 A | 9/1993 | Boivin |
| 5,310,896 A | 5/1994 | Devocelle |
| 5,412,091 A | 5/1995 | Boivin |
| 5,434,258 A | 7/1995 | Devocelle |
| 5,451,690 A | 9/1995 | Devocelle |
| 5,502,183 A | 3/1996 | Andrews |
| 5,502,222 A | 3/1996 | Fu |
| 5,508,452 A | 4/1996 | Roussel |
| 5,616,742 A | 4/1997 | Fu |
| 5,616,743 A | 4/1997 | Boivin |
| 5,731,447 A | 3/1998 | Buendia |
| 5,750,745 A | 5/1998 | Fu |
| 5,939,302 A | 8/1999 | Goeddel |
| 5,972,922 A | 10/1999 | Wilks |
| 5,990,099 A | 11/1999 | Clark |
| 6,011,012 A | 1/2000 | Ni |
| 6,011,023 A | 1/2000 | Clark |
| 6,030,834 A | 2/2000 | Chu |
| 6,090,794 A | 7/2000 | Martuza |
| 6,090,798 A | 7/2000 | Clark |
| 6,169,178 B1 | 1/2001 | La Laggia |
| 6,194,565 B1 | 2/2001 | Buendia |
| 6,500,814 B1 | 12/2002 | Hesch |
| 8,207,151 B2 | 6/2012 | McCall |
| 8,334,279 B2 | 12/2012 | McCall |
| 8,673,887 B2 | 3/2014 | McCall |
| 9,198,921 B2 | 12/2015 | McCall |
| 9,434,758 B2 | 9/2016 | McCall |
| 9,649,320 B2 | 5/2017 | McCall |
| 10,206,933 B2 | 2/2019 | McCall |
| 10,464,967 B2 | 11/2019 | McCall |
| 10,799,514 B2 | 10/2020 | McCall |
| 10,857,161 B2 | 12/2020 | McCall |
| 2002/0002155 A1 | 1/2002 | Bhatnagar |
| 2003/0032630 A1 | 2/2003 | Merlos Roca |
| 2004/0181055 A1 | 9/2004 | Murillo Garrido |
| 2005/0090553 A1 | 4/2005 | Shapiro |
| 2006/0018933 A1 | 1/2006 | Vaya |
| 2006/0024365 A1 | 2/2006 | Vaya |
| 2006/0025436 A1 | 2/2006 | Ridgway |
| 2006/0089395 A1 | 4/2006 | Muto |
| 2006/0153916 A1 | 7/2006 | Vaya |
| 2007/0212751 A1 | 9/2007 | Messinger |
| 2007/0225315 A1 | 9/2007 | Guttridge |
| 2008/0064753 A1 | 3/2008 | Palladino |
| 2008/0090791 A1 | 4/2008 | Reading |
| 2008/0234380 A1 | 9/2008 | Shapiro |
| 2009/0099191 A1 | 4/2009 | Gudkov |
| 2010/0087408 A1 | 4/2010 | McCall |
| 2012/0094970 A1 | 4/2012 | McCall |
| 2013/0079316 A1 | 3/2013 | McCall |
| 2014/0018337 A1 | 1/2014 | Frincke |
| 2014/0142078 A1 | 5/2014 | McCall |
| 2015/0011519 A1 | 1/2015 | McCall |
| 2016/0375037 A1 | 12/2016 | McCall |
| 2017/0027959 A1 | 2/2017 | McCall |
| 2018/0015104 A1 | 1/2018 | McCall |
| 2019/0125763 A1 | 5/2019 | McCall |
| 2020/0148717 A1 | 5/2020 | McCall |
| 2021/0046089 A1 | 2/2021 | McCall |
| 2021/0052606 A1 | 2/2021 | McCall |

FOREIGN PATENT DOCUMENTS

| | | |
|---|---|---|
| CA | 1086715 A | 9/1980 |
| CA | 2725008 | 12/2009 |
| CN | 1896090 A | 1/2007 |
| CN | 1907999 A | 2/2007 |
| CN | 101412742 A | 10/2007 |
| CN | 101347438 A | 1/2009 |
| CN | 101353368 A | 1/2009 |
| CN | 101397319 A | 4/2009 |
| CN | 101397320 A | 4/2009 |
| CN | 101434631 A | 5/2009 |
| CN | 101624414 A | 1/2010 |
| CN | 101759742 | 6/2010 |
| DE | 3149475 A1 | 7/1982 |
| DE | 3227312 A1 | 1/1984 |
| EP | 0057401 A1 | 8/1982 |
| EP | 0097328 A2 | 1/1984 |
| EP | 0114589 A1 | 8/1984 |
| EP | 0126877 A1 | 12/1984 |
| EP | 0156643 A2 | 10/1985 |
| EP | 0164298 A2 | 12/1985 |
| EP | 0263213 A1 | 4/1988 |
| EP | 0875516 A2 | 11/1998 |
| EP | 1236469 | 9/2002 |
| EP | 1236469 A2 | 9/2002 |
| EP | 1336602 A1 | 8/2003 |
| ES | 0445981 A1 | 6/1977 |
| FR | 1433301 | 6/1959 |
| FR | 335 M | 3/1961 |
| GB | 814000 A | 5/1959 |
| GB | 843214 A | 8/1960 |
| GB | 843215 A | 8/1960 |
| GB | 901093 A | 7/1962 |
| GB | 912378 A | 12/1962 |
| GB | 928301 A | 6/1963 |
| GB | 928302 A | 6/1963 |
| GB | 959378 A | 6/1964 |
| GB | 1115893 | 5/1968 |
| GB | 1480763 | 7/1977 |
| GB | 1480763 A | 7/1977 |
| GB | 2089808 A | 6/1982 |
| GB | 2131811 | 6/1984 |
| GB | 2131811 A | 6/1984 |
| JP | H04504572 A | 8/1992 |
| JP | H05500054 A | 1/1993 |
| JP | H05507912 A | 11/1993 |
| JP | 2003081836 | 3/2003 |
| JP | 2009126852 | 6/2009 |
| JP | 5780521 B | 9/2015 |
| RU | 2156256 C1 | 9/2000 |
| WO | 1987001706 | 3/1987 |
| WO | 1987007895 | 12/1987 |
| WO | 1988007092 | 9/1988 |
| WO | 1988007527 | 10/1988 |
| WO | 1988009337 | 12/1988 |
| WO | 1990012577 | 11/1990 |
| WO | 1990015816 | 12/1990 |
| WO | 1991019731 | 12/1991 |
| WO | 1993025570 | 12/1993 |

(56) References Cited

FOREIGN PATENT DOCUMENTS

| WO | 1995018621 | 7/1995 |
|---|---|---|
| WO | 1996006618 | 3/1996 |
| WO | 1996010402 | 4/1996 |
| WO | 1997022616 | 6/1997 |
| WO | 1997039018 | 10/1997 |
| WO | 1999003503 | 1/1999 |
| WO | 1999017778 | 4/1999 |
| WO | 1999032102 | 7/1999 |
| WO | 1999061030 | 12/1999 |
| WO | 2000038653 | 7/2000 |
| WO | 2002000001 | 1/2002 |
| WO | 2002043785 | 6/2002 |
| WO | 2003014141 | 2/2003 |
| WO | 2004012699 | 2/2004 |
| WO | 2006007910 | 1/2006 |
| WO | 2007016979 | 2/2007 |
| WO | 2009155056 | 12/2009 |
| WO | 2010041827 | 4/2010 |
| WO | 2011127048 | 10/2011 |
| WO | 2013082253 | 6/2013 |
| WO | 2017004205 | 1/2017 |

OTHER PUBLICATIONS

U.S. Appl. No. 15/197,118; Notice of Allowance, dated Jun. 4, 2020; 22 pages.

U.S. Appl. No. 16/580,883; Non-Final Office Action, dated Oct. 5, 2020; 37 pages.

U.S. Appl. No. 17/008,237; Application as filed, dated Aug. 31, 2020; 86 pages.

"Duchenne Muscular Dystrophy and Related Dystrophinopathies: Developing Drugs for Treatment Guidance for Industry", FDA Guidance Document issued by the Center for Drug Evaluation and Research, published Feb. 2018; 16 pages.

Fiorillo, A. et al., "Muscle miRNAome Shows Suppression of Chronic InflammatorymiRNAs with Both Prednisone and Vamorolone", Physiol Genomics, 50(9):735-745, (2018).

Fiorillo, A. et al., "TNFα-induced MicroRNAs Control Dystrophin Expression in Becker Muscular Dystrophy", Cell Rep., 12(10): 27 pages, (2015).

Kinder, T. et al., "Muscle Weakness in Myositis: MicroRNA-Mediated Dystrophin Reduction in a Myositis Mouse Model and Human Muscle Biopsies", Arthritis & Rheumatology, 72(7): 1170-1183, (2020).

Liu, X. et al., "Disruption of a key ligand-H-bond network drives dissociative properties in vamorolone for Duchenne muscular dystrophy treatment", Proc. Natl. Acad. Sci. U.S.A., 117(39):24285-93, (2020).

Matthews, E. et al., "Corticosteroids for the treatment of Duchenne muscular dystrophy", Cochrane Database Syst. Rev., 5, (2016).

Mavroudis, P. et al., "Population Pharmacokinetics of Vamorolone (VBP15) in Healthy Men and Boys With Duchenne Muscular Dystrophy", J Clin Pharmacol. 59(7):979-88, (2019).

McDonald, C. et al., "Long-term effects of glucocorticoids on function, quality of life, and survival in patients with Duchenne muscular dystrophy: a prospective cohort study", Lancet, 391(10119):451-61, (2018).

Smith, E. et al., "Efficacy and safety of vamorolone in Duchenne muscular dystrophy: An 18-month interim analysis of a non-randomized open-label extension study", PLOS Med., 17(9): e1003222, (2020).

Ward, L., "Glucocorticoid-Induced Osteoporosis: Why Kids Are Different", Front Endocrinol (Lausanne), 11:576, (2020).

Xiao, L. et al., "New Paradigms in Inflammatory Signaling in Vascular Endothelial Cells", Am J Physiol Heart Circ Physiol, 306:H317-H325, (2014).

U.S. Appl. No. 15/197,118 ; Examiner-Initiated Interview Summary, dated May 20, 2020; 3 pages.

"Heart Failure: Understanding Heart Failure." Cleveland Clinic website. https://my.clevelandclinic.org/health/diseases/17069-heart-failure-understanding-heart-failure. Published Dec. 18, 2017.

Agusti, A., "Systemic Effects of Chronic Obstructive Pulmonary Disease: What We Know and What We Don't Know (But Should)", Proc Am Thorac Soc., 4(7):522-5, (2007).

Asahara, H. et al., "High DNA-Binding Activity of Transcription Factor NF-kappa B in Synovial Membranes of Patients with Rheumatoid Arthritis", Biochem Mol Biol Int., 37(5):827-32, (1995).

Atreya, I. et al., "NF-κB in Inflammatory Bowel Disease", J Inter Med., 263(6):591-6, (2008).

Baeuerle, P. et al., "NF-kB: Ten Years After", Cell, 87(1):13-20, (1996).

Bao, Z. et al., "A Novel Antiinflammatory Role for Andrographolide in Asthma via Inhibition of the Nuclear Factor-kappa B Pathway," Am J Respir Crit Care Med., 179(8):657-65, (2009).

Barnes, P., "The Cytokine Network in Asthma and Chronic Obstructive Pulmonary Disease", J Clin Invest., 118(11):3546-56, (2008).

Bikdeli, B. et al., Two Decades of Cardiovascular Trials With Primal Surrogate Endpoints: 1990-2011, J Am Heart Assoc. 2017; 6:e005285, pp. 1-9.

De Groote, P. et al., "Long-Term Functional and Clinical Follow-Up of Patients With Heart Failure With Recovered Left Ventricular Ejection Fraction After β-Blocker Therapy", Circ. Heart Fail., Downloaded from http://ahajournals.org on Dec. 3, 2018; pp. 434-439, (2014).

Declaration under 37 C.F.R. § 1.132 of John M. McCall, Ph D., dated Feb. 12, 2018; 17 pages.

Definition of "Glioma", American Brain Tumor Association (ABTA), online at http://www.abta.org/brain-tumor-informationtypes-=of-tumors/glioma.html?print=t; accessed Mar. 9, 2016; 3 pages; (2016).

Del Prete, A. et al., "Molecular Pathways in Cancer-Related Inflammation", Biochem Med (Zagreb)., 21(3):264-75, (2011).

Di Meglio, P. et al., "Amelioration of Acute Inflammation by Systemic Administration of a Cell-Permeable Peptide Inhibitor of NF-kB Activation", Arthritis Rheum., 52(3):951-8, (2005).

Di Stefano, A. et al., "Increased Expression of Nuclear Factor-κB in Bronchial Biopsies From Smokers and Patients with COPD", Eur Respir J., 20(3):556-63, (2002).

Edwards, M. et al., "Targeting the NF-κB Pathway in Asthma and Chronic Obstructive Pulmonary Disease", Pharmacol Ther., 121(1):1-13, (2009).

EP Application No. 09767367.7; European Extended Search Report, dated May 12, 2011; 11 pages.

EP Patent Application No. 09767367.7; File History Download, dated Apr. 13, 2012; 219 pages.

EP Patent Application No. 11191434.7; European Search Report, dated Mar. 27, 2012; 12 pages.

EP Patent Application No. 12853185.2; Extended European Search Report, dated Apr. 28, 2015; 12 pages.

Freishtat, R. et al., "Beneficial Glucocorticoid Effects in Asthmatic Airway Epithelium Are Not Dependent on Receptor-Mediated Transcription", Am Fed Med Res., 1 page, (Apr. 2001).

Fukuma, K. et al., "Effect of Lazaroid U-74389G and Methyl prednisolone on Endotoxin-Induced Shock In Mice," Surgery, 125(4):421-30, (1999).

Gong, H. et al., "Dexamethasone Rapidly Inhibits Glucose Uptake via Non-Genomic Mechanisms in Contracting Myotubes", Arch Biochem Biophys., 603:102-9, (2016).

GPG1004 Report and Results, Source: Patent Information Services, Inc. Online Patent and Literature Searching, 113 pages; Apr. 12, 2010.

GPG1017 Report and Results, Source: Patent Information Services, Inc. Online Patent and Literature Searching, 171 pages; Jan. 23, 2011.

GPG903 Report and Results, Source: Patent Information Services, Inc. Online Patent and Literature Searching, 22 pages; Apr. 22, 2009.

GPG903A Report and Results, Source: Patent Information Services, Inc. Online Patent and Literature Searching, 385 pages; Apr. 22, 2009.

(56) References Cited

OTHER PUBLICATIONS

Gulati, G. et al., "Heart Failure With Improved Ejection Fraction: Is it Possible to Escape One's Past?", JACC: Heart Failure, 6(9):725-33, (2018).
Hall, E. et al., "Effects of the 21-Aminosteroid U74006F on Experimental Head Injury in Mice", J Neurosurg., 68(3):456-61, (1988).
Heier, C. et al., "Vamorolone Targets Dual Nuclear Receptors to Treat Inflammation and Dystrophic Cardiomyopathy", Life Science Alliance, 2(1):e201800186, (2019).
Heier, C. et al., "VBP15, A Novel Anti-Inflammatory and Membrane-Stabilizer, Improves Muscle Dystrophy Without Side Effects", EMBO Mol Med, 5(10):1569-85, (2013).
Hori, Y. et al., "Differential Effects of Angiostatic Steroids and Dexamethasone on Angiogenesis and Cytokine Levels in Rat Sponge Implants", Br J Pharmacol., 118(7):1584-91, (1996).
International Application No. PCT/US2009/045489; International Preliminary Report on Patentability, dated Nov. 30, 2010; 7 pages.
International Application No. PCT/US2009/045489; International Search Report and Written Opinion of the International Searching Authority, dated Jan. 29, 2010; 11 pages.
International Application No. PCT/US2012/067003; Declaration of Non-Establishment of International Search Report and Written Opinion of the International Searching Authority, dated Feb. 25, 2013; 4 pages.
International Application No. PCT/US2012/067003; International Preliminiary Report on Patentability, dated Jun. 3, 2014; 4 pages.
International Application No. PCT/US2016/040098; International Preliminary Report on Patentability, dated Jan. 2, 2018; 4 pages.
International Application No. PCT/US2016/040098; International Search Report and Written Opinion of the International Search Authority, dated Sep. 15, 2016; 5 pages.
Izmailova, E. et al., "Use of Molecular Imaging to Quantify Response to IKK-2 Inhibitor Treatment in Murine Arthritis", Arthritis Rheum., 56(1):117-28, (2007).
Jacobsen, J. et al., "Novel 21-Aminosteroids That Inhibit Iron-Dependent Lipid Peroxidation and Protect Against Central Nervous System Trauma", J Med Chem., 33(4):1145-51, (1990).
Jobin, C. et al., "NF-kB Signaling Proteins as Therapeutic Targets for Inflammatory Bowel Diseases", Inflamm Bowel Dis., 6(3):206-13, (2000).
Johnson, J. et al., "Relationships Between Drug Activity and NCI Preclinical In Vitro and In Vivo Models and Early Clinical Trials", Br J Cancer, 84(10):1424-31, (2001).
Kalsi, J. et al., "Suppressive Effects of a Novel Antioxidant Compound on Human T Cell Functions In Vitro", Agents Actions, (Special Conference Issue), 39(Suppl1):C110-C112, (1993).
Kaltschmidt, B. et al., "Activation of NF-κB by Reactive Oxygen Intermediates in the Nervous System", Antioxid Redox Signal., 1(2):129-44, (1999).
Lawrence, T., "The Nuclear Factor NF-kappaB Pathway in Inflammation", Cold Spring Harb Perspect Biol., 1(6):a001651, (2009).
Lin, Y. et al., "Dexamethasone Reduced Invasiveness of Human Malignant Glioblastoma Cells Through a MAPK Phosphatase-1 (MKP-1) Dependent Mechanism", Eur J Pharmacol., 593(1-3):1-9, (2008).
Loprizi, C. et al., "Randomized Comparison of Megestrol Acetate versus Dexamethasone versus Fluoxymesterone for the Treatment of Cancer Anorexia/Cachexia", J Clin Oncol., 17(10):3299-306, (1999).
Louis, D., "Molecular Pathology of Malignant Gliomas", Annu Rev Pathol., 1:97-117, (2006).
Lührs, H. et al., "Butyrate Inhibits NF-κB Activation in Lamina Propria Macrophages of Patients with Ulcerative Colitis", Scand J Gastroenterol., 37(4):458-66, (2002).
Lupón, J. et al., "Recovered Heart Failure With Reduced Ejection Fraction and Outcomes: A Prospective Study", European Journal of Heart Failure, 19:1615-23, (2017).
Maeda, S. et al., "Nod2 Mutation in Crohn's Disease Potentiates NF-κB Activity and IL-1β Processing", Science, 307(57):734-8, (2005).
McGuire, C. et al., "Nuclear Factor Kappa B (NF-.kappa.B) in Multiple Sclerosis Pathology", Trends Mol Med., 19(10):604-13, (2013).
McNatt, L. et al., "Angiostatic Activity of Steroids in the Chick Embryo CAM and Rabbit Cornea Models of Neovascularization", J Ocul Pharmacol Ther., 15(5):413-23, (1999).
Metzinger, L. et al., "Lazaroids Enhance Skeletal Myogenesis in Primary Cultures of Dystrophin-Deficient Mdx Mice", J Neurol Sci., 126(2):138-45, (1994).
Metzinger, L. et al., "Modulation by Prednisolone of Calcium Handling in Skeletal Muscle Cells", Br J Pharmacol., 116(7):2811-6, (1995).
MX Patent Application No. 2010012976; Letter Reporting First Office Action, dated Apr. 3, 2013; 4 pages.
Nadruz, W. et al., "Heart Failure and Midrange Ejection Fraction: Implications of Recovered Ejection Fraction for Exercise Tolerance and Outcomes", Downloaded from http://ahajournals.org on Dec. 3, 2018; pp. 1-8, (2016).
Niazi, S., "Handbook of Pharmaceutical Manufacturing Formulations: Sterile Products", CRC Press LLC, Preface to the Series, 1 page, (2004).
NZ Patent Application No. 589444; Examination Report, dated Dec. 20, 2011; 2 pages.
NZ Patent Application No. 589444; First Official Action, dated Apr. 19, 2011; 2 pages.
NZ Patent Application No. 589444; Response to Office Action, dated Nov. 30, 2011; 35 pages.
NZ Patent Application No. 589444; Second Official Action, dated Oct. 25, 2012; 2 pages.
NZ Patent Application No. 603107; First Official Action, dated Oct. 25, 2012; 2 pages.
NZ Patent Application No. 603107; Specification as filed, dated Oct. 18, 2012; 76 pages.
Onai Y etal., Inhibition of NF-κB improves left ventricular remodeling and cardiac dysfunction after myocardial infarction, Am J Physiol Heart Circ Physiol. Jan. 2007;292(1):H530-H538.
Park, J. et al., "Recurrence of Left Ventricular Dysfunction in Patients With Restored Idiopathic Dilated Cardiomyopathy", Clin Cardiol., 37(4):222-6, (2014).
Peterson, J. et al., "Peptide-Based Inhibitioon of NF-kB Rescues Diaphragm Muscle Contractile Dysfunction in a Murine Model of Duchenne Muscular Dystrophy", Mol Med., 17(5-6):508-15, (2011).
Poynter, M. et al., "NF-kB activation in Airways Modulates Allergic Inflammation but Not Hyperresponsiveness", J Immunol., 173(11):7003-9, (2004).
Pubchem-'668'. Create Date: Aug. 8, 2005 (Aug. 8, 2005) Date Accessed: Aug. 18, 2016 (Aug. 18, 2016); p. 3, compound.
Puliyappadamba, V. et al., "The Role of NF-kappaB in the Pathogenesis of Glioma", Mol Cell Oncol., 1(3):e963478, (2014).
Raychaudhuri, B. et al., "Aberrant Constitutive Activation of Nuclear Factor kB in Glioblastoma Multiforme Drives Invasive Phenotype", J Neurooncol., 85(1):39-47, (2007).
Reeves, E. et al., "VBP15: Preclinical Characterization of a Novel Anti-inflammatory Delta 9, 11 Steroid", Bioorg Med Chem., 21(8):2241-9, (2013).
Ridder, D. et al., "NF-kappaB Signaling in Cerebral Ischemia", Neuroscience, 158(3):995-1006, (2009).
SciFinder search results, (May 28, 2009), 1-20.
Tak, P. et al., "NF-κB: A Key Role in Inflammatory Diseases", J Clin Invest., 107(1):7-11, (2001).
Teramoto, S. et al., "The Role of Nuclear Factor-κB Activation in Airway Inflammation Following Adenovirus Infection and COPD", Chest, 119(4):1294-5, (2001).
U.S. Appl. No. 12/473,921; Notice of Allowance, dated Jan. 20, 2012; 10 pages.
U.S. Appl. No. 12/473,921; Notice of Allowance, dated May 15, 2012; 8 pages.
U.S. Appl. No. 13/327,628; Notice of Allowance, dated Aug. 17, 2012; 9 pages.

(56) References Cited

OTHER PUBLICATIONS

U.S. Appl. No. 13/678,253; Examiner-Initiated Interview Summary, dated Oct. 25, 2013; 1 page.
U.S. Appl. No. 13/678,253; Notice of Allowance, dated Oct. 25, 2013; 12 pages.
U.S. Appl. No. 14/164,779; Notice of Allowance, dated May 5, 2016; 8 pages.
U.S. Appl. No. 14/360,384; Final Office Action, dated Aug. 11, 2017; 16 pages.
U.S. Appl. No. 14/360,384; Final Office Action, dated Mar. 11, 2019; 25 pages.
U.S. Appl. No. 14/360,384; Non-Final Office Action, dated May 18, 2018; 19 pages.
U.S. Appl. No. 14/360,384; Non-Final Office Action, dated Oct. 18, 2016; 15 pages.
U.S. Appl. No. 14/360,384; Notice of Allowability, dated Sep. 25, 2019; 6 pages.
U.S. Appl. No. 14/360,384; Notice of Allowance, dated Jun. 24, 2019; 8 pages.
U.S. Appl. No. 14/360,384; Response After Final Office Action, dated Feb. 12, 2018; 12 pages.
U.S. Appl. No. 14/360,384; Response to Non-Final Office Action, dated Apr. 18, 2017; 6 pages.
U.S. Appl. No. 14/360,384; Response to Restriction Requirement, dated Jul. 26, 2016; 5 pages.
U.S. Appl. No. 15/197,118; Advisory Action, dated Nov. 27, 2017; 3 pages.
U.S. Appl. No. 15/197,118; Applicant-Initiated Interview Summary, dated Dec. 14, 2018; 3 pages.
U.S. Appl. No. 15/197,118; Final Office Action, dated Aug. 17, 2017; 7 pages.
U.S. Appl. No. 15/197,118; Final Office Action, dated Oct. 30, 2018; 14 pages.
U.S. Appl. No. 15/197,118; Non-Final Office Action, dated Apr. 4, 2017; 9 pages.
U.S. Appl. No. 15/197,118; Non-Final Office Action, dated Mar. 22, 2018; 14 pages.
U.S. Appl. No. 15/197,118; Patent Board Decision—Examiner Reversed, dated Feb. 26, 2020; 1 page.
U.S. Appl. No. 15/197,118; Response to Final Office Action, dated Nov. 16, 2017; 8 pages.
U.S. Appl. No. 15/197,118; Response to Non-Final Office Action, dated Aug. 4, 2017; 8 pages.
U.S. Appl. No. 15/229,947; Examiner-Initiated Interview Summary, dated Jan. 10, 2017; 1 page.
U.S. Appl. No. 15/229,947; Notice of Allowance, dated Jan. 10, 2017; 10 pages.
U.S. Appl. No. 15/483,863; Amendment and Response to Non-Final Office Action, dated Jun. 4, 2018; 8 pages.
U.S. Appl. No. 15/483,863; Applicant-Initiated Interview Summary, dated Oct. 3, 2018; 1 page.
U.S. Appl. No. 15/483,863; Final Office Action, dated Aug. 10, 2018; 21 pages.
U.S. Appl. No. 15/483,863; Non-Final Office Action, dated Mar. 5, 2018; 17 pages.
U.S. Appl. No. 15/483,863; Notice of Allowance, dated Oct. 3, 2018; 13 pages.
U.S. Appl. No. 16/226,061; Non-Final Office Action, dated Feb. 5, 2020; 26 pages.
Vernier, A. et al., "Antioxidant Lazaroids Enhance Differentiation of C2 Skeletal Muscle Cells", Neurosci Lett., 186(2-3):177-80, (1995).
Voelkel, N. et al., "Pulmonary Vascular Involvement in Chronic Obstructive Pulmonary Disease", Eur Respir J Supp., 22(46):28-32, (2003).
Voskoglou-Nomikos, T. et al., "Clinical Predictive Value of the in Vitro Cell Line, Human Xenograft, and Mouse Allograft Preclinical Cancer Models", Clin Cancer Res., 9(11):4227-39, (2003).
Weinstein, R. et al., "Promotion of Osteoclast Survival and Antagonism of Bisphosphonate-Induced Osteoclast Apoptosis by Glucocorticoids", J Clin Invest., 109(8):1041-8, (2002).
Weintraub, W. et al., "The Perils of Surrogate Endpoints", Eur Heart J., 36(33):2212-8, (2015).
Wells, E. et al., "Vamorolone, a Dissociative Steroidal Compound, Reduced Pro-Inflammatory Cytokine Expression in Glioma Cells and Increase Activity and Survival in Murine Model of Cortical Tumor", Oncotarget, 8(6):9366-74, (2017).
Yan, J. et al., "NF-κB, A Potential Therapeutic Target For the Treatment of Multiple Sclerosis", CNS Neurol Disord Drug Targets, 7(6):536-57, (2008).
Yang, C. et al., "Immunolocalization of Transcription Factor NF-kappa B in Inclusion-Body Myositis Muscle and at Normal Human Neuromuscular Junctions", Neurosci Lett., 254(2):77-80, (1998).
Zhong, J. et al., "Regulation of Oxygen Free Radical on Expression of Interleukin-8 in Gastric Cancer Cell Line SGC-7901", Zhongguo Zongxiyi Jiehe Waike Zazhi, 12(3):264-8, (2006), Abstract.
"A Study to Assess the Efficacy and Safety of Vamorolone in Boys With Duchenne Muscular Dystrophy (DMD)", ClinicalTrials.gov Identifier: NCT03439670, 16 pages, (first posted: Feb. 20, 2018).
"A Study to Assess Vamorolone in Becker Muscular Dystrophy (BMD)", ClinicalTrials.gov Identifier: NCT05166109, 13 pages, (first posted: Dec. 21, 2021).
"A Study to Assess Vamorolone in Boys Ages 2 to <4 Years and 7 to <18 Years With Duchenne Muscular Dystrophy (DMD)", ClinicalTrials.gov Identifier: NCT05185622, 16 pages, (first posted: Jan. 11, 2022).
"A Study to Assess Vamorolone in Boys With Duchenne Muscular Dystrophy (DMD)", ClinicalTrials.gov Identifier NCT02760264, 12 pages, (first posted: May 3, 2016).
"An Extension Study to Assess Vamorolone in Boys With Duchenne Muscular Dystrophy (DMD)", ClinicalTrials.gov Identifier: NCT02760277, 12 pages, (first posted: May 3, 2016).
"Expanded Access Protocol for Boys With Duchenne Muscular Dystrophy", ClinicalTrials.gov Identifier: NCT03863119, 6 pages, (first posted: Mar. 5, 2019).
"Long-term Extension Study to Assess Vamorolone in Boys With Duchenne Muscular Dystrophy (DMD)", ClinicalTrials.gov Identifier: NCTO3038399, 9 pages, (first posted: Jan. 31, 2017).
"Proof of Concept Trial of Vamorolone in Pediatric Ulcerative Colitis", ClinicalTrials.gov Identifier: NCT04348890, 7 pages, (first posted: Apr. 16, 2020).
Aartsma-Rus, A. et al., "226th ENMC International Workshop: Towards validated and qualified biomarkers for therapy development for Duchenne muscular dystrophy Jan. 20-22, 2017, Heemskerk, The Netherlands", Neuromuscul. Disord., 28(1 ):77-86, (2018).
Benny Klimek, M. et al., "Effects of Chronic, Maximal Phosphorodiamidate Morpholino Oligomer (PMO) Dosing on Muscle Function and Dystrophin Restoration in a Mouse Model of Duchenne Muscular Dystrophy", J. of Neuromuscul. Dis. Preprint: 1-13, (2021).
Clemens, P. et al., "P.337Dystrophin Restoration by Exon 53 Skipping in Patients with Duchenne Muscular Dystrophy After Viltolarsen Treatment: Phase 2 Study Update", Neuromuscl. Disord., 29(1):S165-S166, Abstract, (2019).
Clemens, P. et al., "P.338Vamorolone Trial in Duchenne Muscular Dystrophy Shows Dose-Related Improvement of Muscle Function", Neuromuscul. Dis., 29(1):S166, Abstract, (2019).
Clemens, P. et al., "Drug Development of Vamorolone for Duchenne Muscular Dystrophy", Neuromuscul. Disord., 27 (2):S217-S218, (2017).
Conklin, L. et al., "Developmental Pharmacodynamics and Modeling in Pediatric Drug Development", J. Clin. Pharmacol , 59(1):S87-S94, (2019).
Conklin, L. et al., "Phase IIa Trial in Duchenne Muscular Dystrophy Shows Vamorolone is a First-in-Class Dissociative Steroidal Anti-Inflammatory Drug", Pharmacol. Res., 136:140-150, (2018).
Conklin, L. et al., "Serum Biomarkers of Glucocorticoid Response and Safety in Anti-Neutrophil Cytoplasmic Antibody-Associated Vasculitis and Juvenile Dermatomyositis", Steroids, 140:159-166, (2018).
Conklin, LS et al., "O39 Defining Serum CCL22 and Trefoil Factor 3 (TFF3) as Pharmacodynamic Biomarkers for Use in a Proof-of-Concept Clinical Trial of Vamorolone in Paediatric Ulcerative Colitis", Arch Dis Child, 104:e17, (2019).

(56) References Cited

OTHER PUBLICATIONS

Dang, U. et al., "Serum Biomarkers Associated with Baseline Clinical Severity in Young Steroid-Naive Duchenne Muscular Dystrophy Boys", Human Molecular Genetics, 29(15):2481-2495, (2020).
EMFLAZA™ (Product Label), Prescribing Information, 26 pages, (Revised: Feb. 2017).
Guglieri, M. et al., "P.336Vision DMD: A Phase IIb Randomized, Double-Blind, Parallel Group, Placebo- and Active-Controlled Study to Assess the Efficacy and Safety of Vamorolone in Boys with Duchenne Muscular Dystrophy", Neuromuscul. Dis., 29(1):S165, Abstract, (2019).
Guglieri, M. et al., "Vision DMD: A Drug Development Program for Vamorolone in Duchenne Muscular Dystrophy", Neuromuscul Dis., 1(27):S17, (2017).
Guglieri, M. et al., "Vision DMD: Vamorolone (VBP15) Drug Development Program for Duchenne Muscular Dystrophy", European J. Paediatric Neur., 21(1):E238, Abstract, (2017).
Guglieri, M. et al., "Vamorolone Versus Placebo and Prednisone in Duchenne Muscular Dystrophy: Results from a 24-Week Double-Blind Randomized Trial", Neuromuscul. Dis., 31., (2021).
Guglieri, M., et al., "Vision DMD: Vamorolone Drug Development Program for Duchenne Muscular Dystrophy." Neuromuscul Dis., 26:S156, Abstract, (2016).
Hathout, Y. et al., "Serum Pharmacodynamic Biomarkers for Chronic Corticosteroid Treatment of Children", Scientific Reports, 6:31727, 10 pages, (2016).
Hathout, Y. et al., "Biomarkers for Muscle Disease Gene Therapy", Muscle Gene Therapy, 239-252, (2019).
Hathout, Y. et al., "Disease-Specific and Glucocorticoid-Responsive Serum Biomarkers for Duchenne Muscular Dystrophy", Scientific Reports, 9:12167, 13 pages, (2019).
Hoffman, E. et al., "Clinical Trial Highlights: O. 3a 2.5-Years of Vamorolone Treatment in Duchenne Muscular Dystrophy: Results of an Open Label Long-Term Extension", Neuromuscul. Dis., 31:S48, (2021).
Hoffman, E. et al., "DMD-Treatment: EP. 147 2.5-Years of Vamorolone Treatment in Duchenne Muscular Dystrophy: Results of an Open Label Long-Term Extension", Neuromuscul. Dis., 31:S93-S94, (2021).
Hoffman, E. et al., "Phase 1 Trial of Vamorolone, a First-in-Class Steroid, Shows Improvements in Side Effects via Biomarkers Bridged to Clinical Outcomes", Steroids, 134:43-52 with supplemental materials, 18 pages, (2018).
Hoffman, E. et al., "Phase 1 Trial of Vamorolone, a First-in-Class Steroid, Shows Improvements in Side Effects via Biomarkers Bridged to Clinical Outcomes", Steroids, 134:43-52, (2018).
Hoffman, E. et al., "Vamorolone Trial in Duchenne Muscular Dystrophy Shows Dose-Related Improvement of Muscle Function", Neurology, 93(13):e1312-e1323, (2019).
Hoffman, E., "The Discovery of Dystrophin, The Protein Product of the Duchenne Muscular Dystrophy Gene", The FEBS Journal, 287(18):3879-3887, (2020).
Hoffman, E., "Causes of Clinical Variability in Duchenne and Becker Muscular Dystrophies and Implications for Exon Skipping Therapies", Acta Myologica, 39(4):179-186, (2020).
Hoffman, E., "Pharmacotherapy of Duchenne Muscular Dystrophy", Pediatric Pharmacotherapy, Handbook of Experimental Pharmacology, 25-37, (2019).
Hoffman, P. et al., CCDC Access Structure, Database Identifier SICZIQ, Deposition No. 1557034, retrieved from https://www.ccdc.cam.ac.uk/structures/Search?Ccdcid=1557034&DatabaseToSearch= Published on Mar. 14, 2022; 5 pages, (deposited on Jun. 19, 2017).
Li, X. et al., "Exposure-Response Analysis of Vamorolone (VBP15) in Boys With Duchenne Muscular Dystrophy", J. Clin. Pharmacol., 60(10): 1385-1396, (2020).
Mah, J. et al., "Efficacy and Safety of Vamorolone in Duchenne Muscular Dystrophy: A 30-Month Nonrandomized Controlled Open-Label Extension Trial", JAMA Network Open, 5(1):e2144178, 16 pages, (2022).
Mah, J. et al., "Vamorolone Versus Corticosteroid Real-World Experience: Comparisons of 2-Year Treatment Period with Northstar UK Network and CINRG Duchenne Natural History Study", Neuromuscul. Dis., 31, (2021).
Nagaraju, K. et al., "DMD Clinical Therapies I: P.114Vamorolone as a Replacement for Corticosteroids in Duchenne Muscular Dystrophy: Phase 2a Results in 48 DMD Boys", Neuromuscul. Dis., 28:S63-S64, (2018).
RAYOS (Product Label), Prescribing Information, 16 pages, (Revised: Jul. 2012).
Roy, R. et al., "Acute Serum Protein and Cytokine Response of Single Dose of Prednisone in Adult Volunteers", Steroids, 178(2): 108953, 9 pages, (2022).
Smith, E. et al., "Vamorolone Newsletter #1", ReverGen BioPharma, 1(1):1-6, (2017).
Sreetama, S. et al., "Membrane Stabilization by Modified Steroid Offers a Potential Therapy for Muscular Dystrophy Due to Dysferlin Deficit", Molecular Therapy, 26(9):2231-2242, (2018).
Takeda, S. et al., "Exon-Skipping in Duchenne Muscular Dystrophy", Journal of Neuromuscular Diseases, 8:S343-S358, (2021).
Ward, L. et al., "Proceedings of a Parent Project Muscular Dystrophy Bone Health Workshop: Morbidity due to osteoporosis in DMD: The Path Forward May 12-13, 2016, Bethesda, Maryland, USA", Neuromuscular Disorders, 28 (1):64-76, (2018).
Ziemba, M. et al., "Biomarker-Focused Multi-Drug Combination Therapy and Repurposing Trial in MDX Mice", PloS One, 16(2):e0246507, 19 pages, (2021).

AQUEOUS ORAL PHARMACEUTICAL SUSPENSION COMPOSITIONS

This application claims the benefit of priority of U.S. Provisional Patent Application Ser. No. 62/815,097 filed Mar. 7, 2019, the disclosure of which is incorporated by reference in its entirety for all purposes.

Vamorolone is a synthetic glucocorticoid corticosteroid, also known as VB-15, VBP-15, 16α-methyl-9,11-dehydroprednisolone, or 17α,21-dihydroxy-16α-methylpregna-1,4,9(11)-triene-3,20-dione:

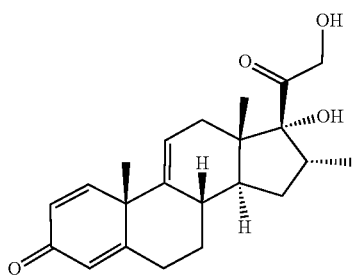

Pre-clinical data have shown that vamorolone binds potently to the glucocorticoid receptor and has anti-inflammatory effects similar to traditional glucocorticoid drugs. Testing of multiple mouse models of inflammatory states has shown efficacy similar to prednisolone, and dramatically improves side effect profiles, including loss of growth stunting and loss of bone fragility.

Provided is an aqueous oral pharmaceutical suspension composition comprising vamorolone Form I. Also provided is an aqueous oral pharmaceutical suspension composition comprising: vamorolone Form I; at least one suspending agent; and at least one suspension vehicle. Also provided are methods for preparing such suspensions as well as methods for their use in methods of treating or reducing the symptoms of muscular dystrophy.

These and other aspects of the invention disclosed herein will be set forth in greater detail as the patent disclosure proceeds.

DETAILED DESCRIPTION

Figure 1:
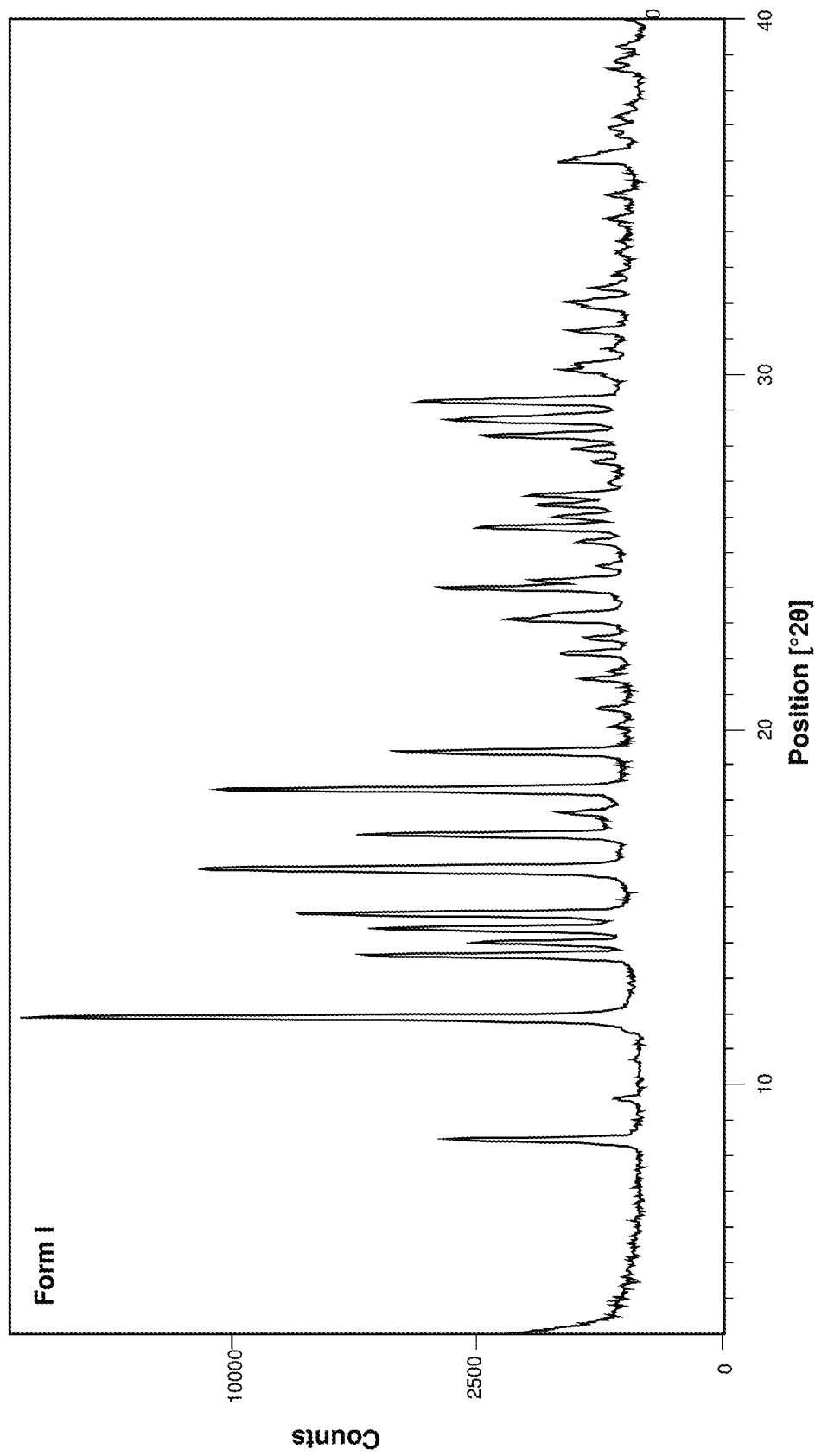
FIG. 1 shows a pXRD pattern of vamorolone Form I.

As used in the present specification, the following words and phrases are generally intended to have the meanings as set forth below, except to the extent that the context in which they are used indicates otherwise.

VAMOROLONE: As used herein, "vamorolone" refers to 17α,21-dihydroxy-16α-methylpregna-1,4,9(11)-triene-3,20-dione (also known as VBP15) and has the structure:

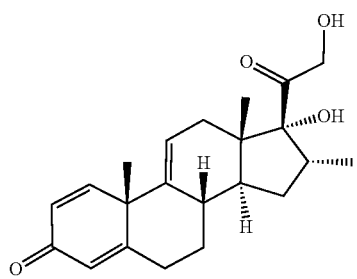

POLYMORPHS AND POLYMORPHIC FORMS: Vamorolone can exist as various polymorphic forms. As used herein, the terms, "polymorphs" and "polymorphic forms" and related terms herein refer to crystalline forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can also result from changes in chemical reactivity (e.g., differential oxidation, such that a dosage form discolors more rapidly when comprised of one polymorph than when comprised of another polymorph) or mechanical property (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g., IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

To "characterize" a solid form of a compound, one may, for example, collect XRPD data on solid forms of the compound and compare the XRPD peaks of the forms. For example, when only three solid forms, e.g., Forms X and Y and Material N, are compared and the Form X pattern shows a peak at an angle where no peaks appear in the Form Y or Material N pattern, then that peak, for that compound, distinguishes Form X from Form Y and Material N and further acts to characterize Form X. The collection of peaks which distinguish e.g., Form X from the other known forms is a collection of peaks which may be used to characterize Form X. Those of ordinary skill in the art will recognize that there are often multiple ways, including multiple ways using the same analytical technique, to characterize solid forms. Additional peaks could also be used, but are not necessary, to characterize the form up to and including an entire diffraction pattern. Although all the peaks within an entire XRPD pattern may be used to characterize such a form, a subset of that data may, and typically is, used to characterize the form.

An XRPD pattern is an x-y graph with diffraction angle (typically ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2°2θ to diffraction angles in XRPD patterns.

ABOUT: As used herein, the term "about" is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

ADMINISTERING: As used herein, "administering" means to provide a compound or other therapy, remedy, or treatment such that an individual internalizes a compound.

DISEASE: As used herein, the term "disease" is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

IN NEED OF TREATMENT and IN NEED THEREOF: As used herein, "in need of treatment" and "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

NF-κB-MEDIATED DISEASE: As used herein, the term "NF-κB-mediated disease" refers to a disease having a significant and pathologic inflammatory component that can be addressed by inhibition of NF-κB. The disease may be completely or partially mediated by modulating the activity or amount of NF-κB. In particular, the disease is one in which modulation of NF-κB results in some effect on the underlying disease e.g., administration of a NF-κB modulator results in some improvement in at least some of the patients being treated. The term "NF-κB-mediated disease" also refers to the following diseases, even though the compounds disclosed herein exert their effects through biological pathways and/or processes other than NF-κB: muscular dystrophy, arthritis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, and hearing loss.

PHARMACEUTICAL COMPOSITION: As used here, "pharmaceutical composition" means a composition comprising at least one active ingredient, such as vamorolone or a polymorphic form thereof, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

PURE: As used herein, the term "pure" means about 90-100%, preferably 95-100%, more preferably 98-100% (wt/wt) or 99-100% (wt/wt) pure compound; e.g. less than about 10%, less than about 5%, less than about 2% or less than about 1% impurity is present. Such impurities include, e.g., degradation products, oxidized products, epimers, solvents, and/or other undesirable impurities.

RANGES: When ranges of values are disclosed, and the notation "from $n_1$ . . . to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

ROOM TEMPERATURE: As used herein, the term "room temperature" refers to a temperature of 68 to 86 F.

STABLE: As used herein, the term "stable" refers to both chemical (shelf-life) and physical stability (suspension uniformity). Improved uniformity results in an improved product because less shaking of the suspension is required before dosing and allows the product to be stored longer (i.e. longer shelf-life) because the drug in the product will not settle and compact.

SUSPENSION: As used herein, the term "suspension" refers to a mixture of a solid in liquid. In contrast, an "emulsion" refers to a mixture of two immiscible liquids.

THERAPEUTICALLY ACCEPTABLE: As used herein, the term "therapeutically acceptable" refers to those compounds (or salts, prodrugs, tautomers, zwitterionic forms, etc.) suitable for use in contact with the tissues of patients without undue toxicity, irritation, and allergic response, are commensurate with a reasonable benefit/risk ratio, and are effective for their intended use.

THERAPEUTICALLY EFFECTIVE: As used herein, the phrase "therapeutically effective" is intended to qualify the amount of active ingredients used in the treatment of a disease or disorder. This amount will achieve the goal of reducing or eliminating the disease or disorder.

TREATMENT: As used herein, "treating," "treatment," and the like means ameliorating a disease so as to reduce or eliminate its cause, its progression, its severity, or one or more of its symptoms, or otherwise beneficially alter the disease in a subject. Treatment may also be preemptive in nature, i.e., it may include prophylaxis of disease in a subject exposed to or at risk for the disease. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps, or group of compositions of matter shall be taken to encompass one and a plurality (i.e. one or more) of those steps, compositions of matter, groups of steps, or groups of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of steps or features unless specifically stated otherwise.

The present invention(s) is not to be limited in scope by the specific embodiments described herein, which are intended for the purpose of exemplification only. Functionally-equivalent products, compositions, and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination.

Aqueous Oral Pharmaceutical Suspension

Provided is an aqueous oral pharmaceutical suspension composition comprising vamorolone Form I. Also provided is an aqueous oral pharmaceutical suspension composition comprising: vamorolone Form I; at least one suspending agent; and at least one suspension vehicle.

In some embodiments, the aqueous oral pharmaceutical suspension composition comprises vamorolone Form I in an amount of between about 2% and about 10% w/w. In some embodiments, the aqueous oral pharmaceutical suspension composition comprises vamorolone Form I in an amount of between about 2% and about 9% w/w. In some embodiments, the aqueous oral pharmaceutical suspension composition comprises vamorolone Form I in an amount of between about 2% and about 8% w/w. In some embodiments, the aqueous oral pharmaceutical suspension composition comprises vamorolone Form I in an amount of between about 2% and about 7% w/w. In some embodiments, the aqueous oral pharmaceutical suspension composition comprises vamorolone Form I in an amount of between about 3% and about 5% w/w. In some embodiments, the aqueous oral pharmaceutical suspension composition comprises vamorolone Form I in an amount of about 4% w/w.

In some embodiments, vamorolone Form I is characterized by an X-ray powder diffraction pattern comprising peaks, in terms of ° 2θ, at about 11.9, about 13.7, about 16.1, and about 18.3 with radiation Cu Kα. In some embodiments, vamorolone Form I is characterized by an X-ray powder diffraction pattern comprising peaks, in terms of ° 2θ, at about 11.9, about 13.7, about 14.4, about 14.8, about 16.1, about 17.0, and about 18.3 with radiation Cu Kα. In some embodiments, vamorolone Form I is characterized by an X-ray powder diffraction pattern substantially as shown in FIG. 1.

Figure 2:
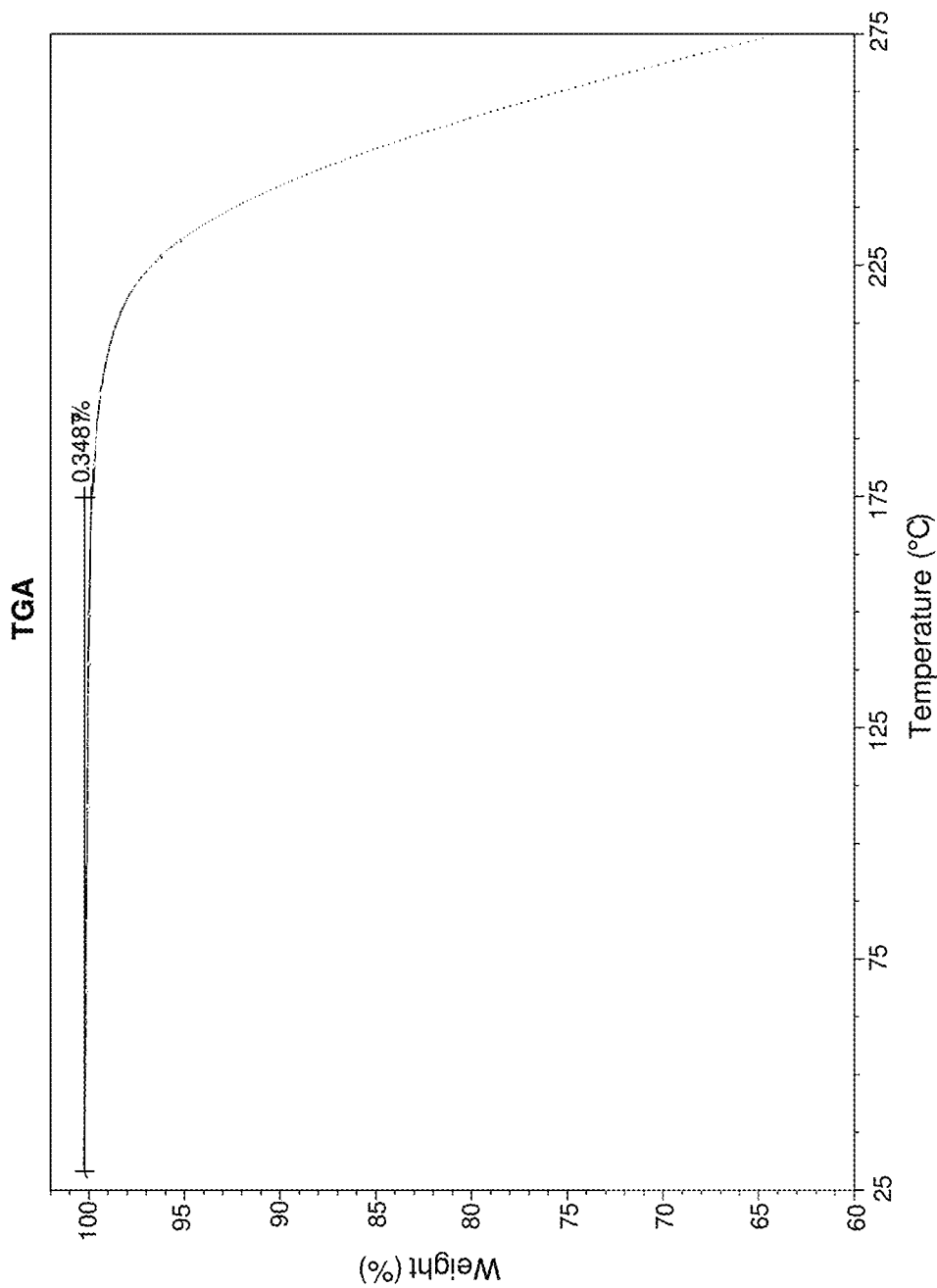
FIG. 2 shows a TGA profile of vamorolone Form I.

In some embodiments, vamorolone Form I is characterized by a thermogravimetric analysis profile showing less than about 0.5% weight loss below about 175° C. In some embodiments, vamorolone Form I is characterized by a thermogravimetric analysis profile substantially as shown in FIG. 2.

Figure 3:
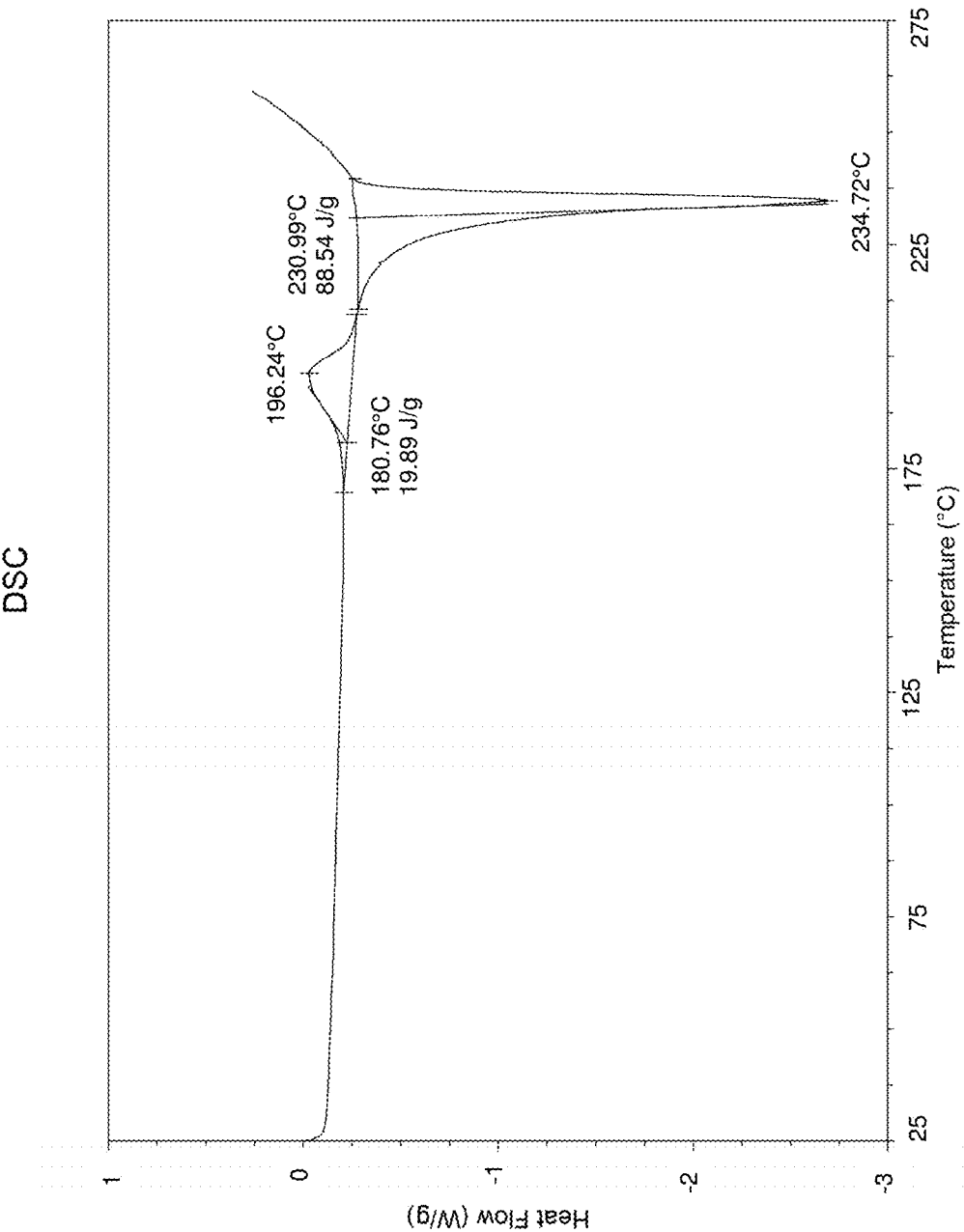
FIG. 3 shows a DSC profile of vamorolone Form I.

In some embodiments, vamorolone Form I is characterized by an exothermic event onset at 180.7° C. and a melting event with an onset and peak temperatures of 231.0° C. and 234.7° C., respectively, as measured by differential scanning calorimetry. In some embodiments, vamorolone Form I is characterized by a differential scanning calorimetry trace substantially as shown in FIG. 3.

In some embodiments, vamorolone Form I has a chemical purity of at least about 95%, at least about 96%, at least about 97%, at least about 98%, at least about 99%, or at least about 99.5% by high performance liquid chromatography. In some embodiments, vamorolone Form I has total chemical impurities of not more than about 0.5%, not more than about 0.4%, not more than about 0.3%, not more than about 0.2%, or not more than about 0.1%, by high performance liquid chromatography.

In some embodiments, vamorolone Form I has a particle size such that $d_{90}$ is less than about 50 am, less than about 40 am, or less than about 30 am. In some embodiments, vamorolone Form I has a particle size such that $d_{50}$ is less than about 30 am, less than about 20 am, between about 10 and about 20 am, or between about 14 and about 17 am. In some embodiments, vamorolone Form I has a particle size such that $d_{50}$ is less than about 20 am, less than about 10 am, between about 5 and about 10 am, or between about 5 and about 6.5 m.

In some embodiments, the suspending agent is chosen from acacia, agar, alginic acid or a salt thereof, bentonite, carbomers, carboxymethylcellulose or a salt thereof, carrageenan, corn starch, ethylcellulose, gelatin, guar gum, hydroxyethylcellulose, hydroxyethylmethylcellulose, hydroxypropyl cellulose, hydroxypropylmethylcellulose, methylcellulose, microcrystalline cellulose, pectin, polyvinyl alcohol, polyvinyl pyrrolidone, polyethylene oxide, colloidal silicon dioxide, tragacanth, xanthan gum, and mixtures thereof.

In some embodiments, the suspending agent is chosen from carboxymethylcellulose or a salt thereof, microcrystalline cellulose, xanthan gum, and mixtures thereof.

In some embodiments, the suspending agent comprises a mixture of microcrystalline cellulose, xanthan gum, and carboxymethylcellulose, or a salt thereof.

In some embodiments, the suspending agent comprises a mixture of microcrystalline cellulose, xanthan gum, and sodium carboxymethylcellulose.

In some embodiments, the at least one suspending agent is present in an amount of between about 0.1% to about 5% w/w, such as between about 0.1% to about 0.5% w/w, for example, between about 0.2% to about 0.4% w/w. In certain embodiments, the at least one suspending agent comprises xanthan gum present in the amount of between about 0.2% and about 0.4%.

In some embodiments, the at least one suspending agent is present in an amount of between about 0.5% to about 5% w/w, such as between about 0.5% to about 4% w/w, for example, between about 1% to about 3% w/w.

In some embodiments, the suspension vehicle is chosen from a sweetener (e.g. a sugar, sugar substitute, or sugar alcohol) or low molecular weight polyol. In some embodiments, the suspension vehicle is chosen from xylitol, propylene glycol, glycerin, sorbitol, liquid glucose, dextrose, and mixtures thereof. In some embodiments, the suspension vehicle is propylene glycol, dextrose, or a mixture thereof. In some embodiments, the suspension vehicle is a mixture of propylene glycol and dextrose.

In some embodiments, the suspension vehicle is present in an amount of between about 0.1% to about 10% w/w. In some embodiments, the suspension vehicle is present in an amount of between about 3% to about 10% w/w. In some embodiments, the suspension vehicle is present in an amount of between about 4% to about 8% w/w. In some embodiments, the suspension vehicle is present in an amount of between about 5% to about 7% w/w. In some embodiments, the suspension vehicle is present in an amount of about 6% w/w.

In some embodiments, the aqueous oral pharmaceutical suspension composition further comprises at least one surfactant. In some embodiments, the surfactant is chosen from an alkyl aryl polyether polymer, a polyoxyethylene polyoxypropylene polymer, polysorbates, polyoxyl 35 castor oil, polyoxyl 40 hydrogenated castor oil, polyoxyl 40 stearates, sorbitan monolaureates, poloxamer and combinations thereof. In some embodiments, the surfactant is a polysorbate. In some embodiments, the surfactant is polysorbate 80.

In some embodiments, the surfactant is present in amount of between about 0.01% to about 1% w/w. In some embodiments, the surfactant is present in an amount of between about 0.01% to about 0.5% w/w. In some embodiments, the surfactant is present in an amount of between about 0.05% to about 0.2% w/w. In some embodiments, the surfactant is present in an amount of about 0.1% w/w.

In some embodiments, the aqueous oral pharmaceutical suspension composition further comprises at least one preservative. In some embodiments, the preservative is chosen from benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, sodium methyl paraben, methyl paraben, sodium propyl paraben, thimerosal, sodium benzoate, benzalkonium chloride, potassium sorbate, and mixtures thereof. In some embodiments, the preservative is methylparaben, sodium benzoate, or a mixture thereof. In some embodiments, the preservative is a mixture of methylparaben and sodium benzoate.

In some embodiments, the at least one preservative is present in an amount of between about 0.1% and about 1% w/w. In some embodiments, the at least one preservative is present in an amount of between about 0.1% and about 0.5% w/w. In some embodiments, the at least one preservative is present in an amount of about 1% w/w. In some embodiments, the at least one preservative is present in an amount of about 0.1% w/w. In some embodiments, the at least one preservative is present in an amount of about 0.2% w/w.

In some embodiments, the aqueous oral pharmaceutical suspension composition further comprises at least one stabilizing agent. In some embodiments, the stabilizing agent is ethylenediaminetetraacetic acid (EDTA).

In some embodiments, the aqueous oral pharmaceutical suspension composition further comprises a buffer. In some embodiments, the buffer is sufficient to neutralize the suspension to a pH of about 4 and 5. In some embodiments, the buffer is sufficient to neutralize the suspension to a pH of about 4.5 and 5.5. In some embodiments, the buffer is sufficient to neutralize the suspension to a pH of about 4. In some embodiments, the buffer is sufficient to neutralize the suspension to a pH of about 5.

In some embodiments, the aqueous oral pharmaceutical suspension composition further comprises a flavoring agent. As vamorolone has a fairly neutral taste, as opposed to prednisolone which tastes bitter, the addition of a flavoring agent is useful to make the suspension even more palatable.

In some embodiments, the aqueous oral pharmaceutical suspension composition comprises between 3.6% and 4.4% w/w vamorolone Form I, between 0.4% and 0.6% w/w sodium carboxymethyl cellulose, between 0.1% and 2% w/w xanthan gum, between 0.8% and 1.2% w/w dextrose, between 0.05% and 0.15% w/w polysorbate 80, between 1.7% and 2.7% w/w microcrystalline cellulose, between 0.1% and 0.3% w/w dibasic sodium phosphate, between 0.1% and 0.3% w/w citric acid, between 0.05% and 0.15% w/w methylparaben, between 0.05% and 0.15% w/w sodium benzoate, between 4% and 6% w/w glycerin, between 0.05% and 0.15% w/w flavoring, and between 83% and 89% w/w water.

In some embodiments, the aqueous oral pharmaceutical suspension composition comprises about 4% w/w vamorolone Form I, about 0.5% w/w sodium carboxymethyl cellulose, about 0.15% w/w xanthan gum, about 1.0 w/w % dextrose, about 0.1% w/w polysorbate 80, about 2.2% w/w microcrystalline cellulose, about 0.2% w/w dibasic sodium phosphate, about 0.2% w/w citric acid, about 0.1% w/w methylparaben, about 0.1% w/w sodium benzoate, about 5% w/w glycerin, about 0.1% w/w flavoring, and about 86.4% w/w water.

In some embodiments, the aqueous oral pharmaceutical suspension composition comprises between 3.6% and 4.4% w/w vamorolone Form I, between 0.4% and 0.6% w/w sodium carboxymethyl cellulose, between 0.1% and 2% w/w xanthan gum, between 0.8% and 1.2% w/w dextrose, between 0.05% and 0.15% w/w polysorbate 80, between 0.5% and 0.8% w/w microcrystalline cellulose, between 0.1% and 0.3% w/w dibasic sodium phosphate, between 0.1% and 0.3% w/w citric acid, between 0.05% and 0.15% w/w methylparaben, between 0.05% and 0.15% w/w sodium benzoate, between 4% and 6% w/w propylene glycol, between 0.05% and 0.15% w/w flavoring, and between 83% and 89% w/w water.

In some embodiments, the aqueous oral pharmaceutical suspension composition comprises about 4% w/w vamorolone Form I, about 0.5% w/w sodium carboxymethyl cellulose, about 0.15% w/w xanthan gum, about 1.0% w/w dextrose, about 0.1% w/w polysorbate 80, about 0.6% w/w microcrystalline cellulose, about 0.2% w/w dibasic sodium phosphate, about 0.2% w/w citric acid, about 0.1% w/w methylparaben, about 0.1% w/w sodium benzoate, about 5% w/w propylene glycol, about 0.1% w/w flavoring, and about 86.4% w/w water.

In some embodiments, the aqueous oral pharmaceutical suspension composition comprises 3-5% w/w vamorolone Form I, 2-3% w/w dextrose, 0.1-0.2% w/w carboxymethyl cellulose, 1-1.5% microcrystalline cellulose, 0.2-0.4% w/w dibasic sodium phosphate, 0.1-0.3% w/w citric acid, 0.4-0.6% w/w sodium benzoate, 0.1-0.3% w/w potassium sorbate, 0.05-0.2% w/w EDTA, 4-6% w/w glycerin, 0.05-0.2% w/w flavoring, and the remainder water.

In some embodiments, the aqueous oral pharmaceutical suspension composition comprises about 4% w/w vamorolone Form I, about 1% w/w dextrose, about 0.05% w/w carboxymethyl cellulose (e.g., about 0.045% w/w high viscosity), about 1.2% microcrystalline cellulose, about 0.3% w/w dibasic sodium phosphate (e.g., about 0.28% w/w), about 0.2% w/w citric acid (e.g. about 0.21% w/w), about 0.5% w/w sodium benzoate, about 0.2% w/w potassium sorbate, about 0.1% w/w EDTA, about 5% w/w glycerin, about 0.1% w/w flavoring, and the remainder water.

In some embodiments, the aqueous oral pharmaceutical suspension composition comprises 3-5% w/w vamorolone Form I, 0.05-0.2% w/w sucralose, 0.2-0.4% w/w xanthan gum, 0.2-0.4% w/w dibasic sodium phosphate, 0.1-0.3% w/w citric acid, 0.4-0.6% w/w sodium benzoate, 0.1-0.3% w/w potassium sorbate, 0.05-0.2% w/w EDTA, 4-6% w/w glycerin, about 0.05-0.2% w/w flavoring, and the remainder water.

In some embodiments, the aqueous oral pharmaceutical suspension composition comprises about 4% w/w vamorolone Form I, about 0.1% w/w sucralose, about 0.3% w/w xanthan gum, about 0.3% w/w dibasic sodium phosphate (e.g., about 0.28% w/w), about 0.2% w/w citric acid (e.g. about 0.21% w/w), about 0.5% w/w sodium benzoate, about 0.2% w/w potassium sorbate, about 0.1% w/w EDTA, about 5% w/w glycerin, about 0.1% w/w flavoring, and the remainder water.

In some embodiments, the aqueous oral pharmaceutical suspension composition comprises 3-5% w/w vamorolone Form I, 0.05-0.2% w/w sucralose, 0.2-0.4% w/w xanthan gum, 0.2-0.4% w/w dibasic sodium phosphate, 0.1-0.3% w/w citric acid, 0.05% w/w-0.3% w/w sodium benzoate, 4-6% w/w glycerin, 0.05-0.2% w/w flavoring, and the remainder water.

In some embodiments, the aqueous oral pharmaceutical suspension composition comprises about 4% w/w vamorolone Form I, about 0.1% w/w sucralose, about 0.3% w/w xanthan gum, about 0.3% w/w dibasic sodium phosphate (e.g., about 0.28% w/w), about 0.2% w/w citric acid (e.g. about 0.21% w/w), about 0.2% w/w-0.1% w/w sodium benzoate, about 5% w/w glycerin, about 0.1% w/w flavoring, and the remainder water.

In some embodiments, the aqueous oral pharmaceutical suspension composition comprises 3-5% w/w vamorolone Form I, 2-3% w/w dextrose, 0.1-1% w/w carboxymethyl cellulose, 0.1-0.2% w/w xanthan gum, 1-1.5% microcrystalline cellulose, 0.1-0.3% w/w dibasic sodium phosphate, 0.1-0.3% w/w citric acid, 0.05-0.3% methylparaben, 0.1-0.3% w/w sodium benzoate, 4-6% w/w glycerin, 0.05-0.2% w/w flavoring, and the remainder water.

In some embodiments, the aqueous oral pharmaceutical suspension composition comprises about 4% w/w vamorolone Form I, about 1% w/w dextrose, about 0.5% w/w carboxymethyl cellulose, about 0.15% w/w xanthan gum, about 1.2% microcrystalline cellulose, about 0.2% w/w dibasic sodium phosphate (e.g., about 0.19% w/w), about 0.2% w/w citric acid (e.g. about 0.19% w/w), about 0.1% methylparaben, about 0.2% w/w sodium benzoate, about 5.0% w/w glycerin, about 0.1% w/w flavoring, and the remainder water.

In some embodiments, the aqueous oral pharmaceutical suspension composition comprising vamorolone Form I exhibits extended shelf life stability. The shelf life may be up to about six months, twelve months, eighteen months, twenty-four months, thirty months, or thirty-six months.

In some embodiments, the aqueous oral pharmaceutical suspension composition comprising vamorolone Form I is stable at 25° C./60% relative humidity for at least three months, at least four months, at least five months, at least six months, at least seven months, at least eight months, at least nine months, at least ten months, at least eleven months, at least one year, or at least two years.

In some embodiments, the aqueous oral pharmaceutical suspension composition comprising vamorolone Form I has total chemical impurities of not more than about 2%, not more than about 1.5%, not more than about 1%, not more than about 0.9%, not more than about 0.8%, not more than about 0.7%, not more than about 0.6%, or not more than about 0.55%, by high performance liquid chromatography.

In some embodiments, the aqueous oral pharmaceutical suspension composition comprising vamorolone Form I has not more than about 0.5%, not more than about 0.4%, not more than about 0.3%, not more than about 0.2%, or not more than about 0.1%, by high performance liquid chromatography of any individual impurity.

In some embodiments, the aqueous oral pharmaceutical suspension composition comprising vamorolone Form I has not more than about 0.5%, not more than about 0.4%, not more than about 0.3%, not more than about 0.2%, or not more than about 0.1%, by high performance liquid chromatography of an epoxide having the formula:

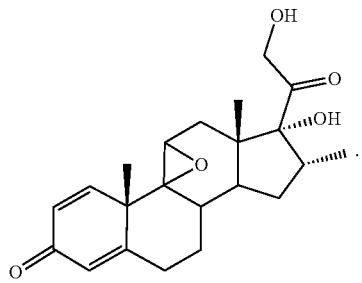 [SMILES: C[C@@H]1CC2C3CCC4=CC(=O)C=C[C@]4(C)C34OC4C[C@]2(C)[C@@]1(O)C(=O)CO]

In some embodiments, the aqueous oral pharmaceutical suspension composition comprising vamorolone Form I has not more than about 0.5%, not more than about 0.4%, not more than about 0.3%, not more than about 0.2%, or not more than about 0.15%, by high performance liquid chromatography of a ketone having the formula:

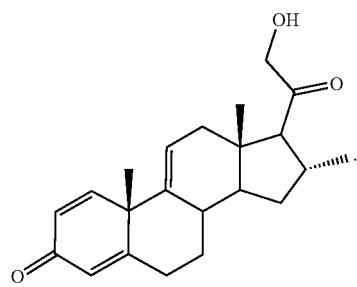 [SMILES: C[C@@H]1CC2C3CCC4=CC(=O)C=C[C@]4(C)C3=CC[C@]2(C)C1C(=O)CO]

The ketone impurity is also referred to as the impurity having a relative retention time of 1.27-1.28.

In some embodiments, the aqueous oral pharmaceutical suspension composition comprising vamorolone Form I has not more than about 0.5%, not more than about 0.4%, not more than about 0.3%, not more than about 0.2%, or not more than about 0.16%, by high performance liquid chromatography of a diastereomeric compound having the formula:

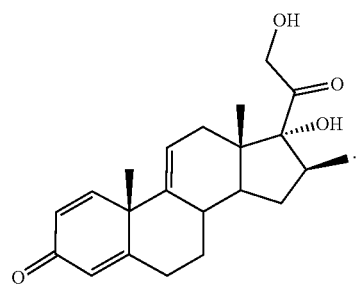 [SMILES: C[C@H]1CC2C3CCC4=CC(=O)C=C[C@]4(C)C3=CC[C@]2(C)[C@@]1(O)C(=O)CO]

The ketone impurity is also referred to as the impurity having a relative retention time of 1.05.

In some embodiments, the aqueous oral pharmaceutical suspension composition comprising vamorolone Form I has not more than about 0.5%, not more than about 0.4%, or not more than about 0.3%, by high performance liquid chromatography of an acetate having the formula:

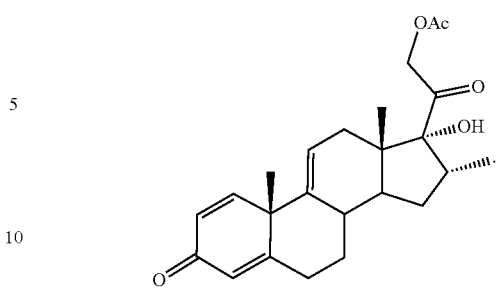

The acetate impurity is also referred to as the impurity having a relative retention time of 1.38-1.40.

Methods of Use

Also provided are methods for treating a disease having a significant and pathologic inflammatory component that can be addressed by inhibition of NF-κB in a human or animal subject in need of such treatment comprising administering to the subject an amount of a suspension described herein effective to reduce or prevent the disease in the subject, optionally in combination with at least one additional agent for the treating the disease that is known in the art.

Specific diseases to be treated by the compounds, compositions, and methods disclosed herein include acid-induced lung injury, acne (PAPA), acute respiratory distress syndrome, ageing, AIDS, HIV-1, alcoholic hepatitis, alcoholic liver disease, allergic bronchpulmonay aspergillosis, Alzheimer's disease, amyotropic lateral sclerosis, angina pectoris, anhidrotic ecodermal dysplasia-ID, ankylosing spondylitis, antiphospholipid syndrome, aphthous stomatitis, appendicitis, arthritis, asthma, allergen induced asthma, non-allergen induced asthma, atherosclerosis, atopic dermatitis, autoimmune diseases, Behcet's disease, Bell's palsy, Blau syndrome, bronchiolitis, cancer, cardiac hypertrophy, catabolic disorders, cataracts, cerebral aneurysm, chronic heart failure, chronic lung disease (including of prematurity), chronic obstructive pulmonary disease, colitis, ulcerative colitis, complex regional pain syndrome, connective tissue diseases, crohn's disease, cryopyrin-associated periodic syndromes, cyrptococcosis, cystic fibrosis, deficiency of the interleukin-1-receptor antagonist (DIRA), dermatitis, dermatomyositis, endometriosis, endotoxemia, familial amyloidotic polyneuropathy, familial cold urticaria, familial mediterranean fever, fetal growth retardation, glaucoma, glomerular disease, glomerular nephritis, gut diseases, head injury, headache, hearing loss, heart disease, Henoch-Scholein purpura, hepatitis, hereditary periodic fever syndrome, herpes zoster and simplex, Huntington's disease, hyaline membrane disease, hypercholesterolemia, hyperimmunoglobulinemia D with recurrent fever (HIDS), hypoplastic and other anemias, incontinentia pigmenti, infectious mononucleosis, inflammatory bowel disease, inflammatory lung disease, inflammatory neuropathy, inflammatory pain, irritant-induced inflammation, plant irritant-induced inflammation, poison ivy/urushiol oil-induced inflammation, chemical irritant-induced inflammation, bee sting-induced inflammation, insect bite-induced inflammation, ischemia/reperfusion, kidney disease, kidney injury caused by parasitic infections, leptospiriosis, leukemia, lung injury, lupus, lupus nephritis, lymphoma, meningitis, mesothelioma, Muckle-Wells syndrome (urticaria deafness amyloidosis), multiple sclerosis, muscle wasting, muscular dystrophy, mycosis fungoides, myelodysplastic syndrome, myocarditis, myositis, nasal sinusitis, necrotizing enterocolitis, neonatal onset multisystem inflammatory disease (NOMID), nephrotic syndrome, neuritis, neuropathological diseases, obesity, ocular allergy, osteoarthritis, otitis media, Paget's disease, pain, pancreatitis, Parkinson's disease, pericarditis, periodic fever, periodontitis, peritoneal endometriosis, pertussis, pharyngitis and adenitis (PFAPA syndrome), pneumosystis infection, polyarteritis *nodosa*, polycystic kidney disease, polymyositis, psoriasis, psychosocial stress diseases, pulmonary disease, pulmonary fibrosis, pulmonary hypertension, pyoderma gangrenosum, pyogenic sterile arthritis, renal disease, retinal disease, rheumatic disease, rheumatoid arthritis, sarcoidosis, sebborrhea, sepsis, silica-induced diseases, Sjogren's syndrome, skin diseases, sleep apnea, solid tumors, spinal cord injury, stroke, subarachnoid hemorrhage, sunburn, burns, thrombocytopenia, TNF receptor associated periodic syndrome (TRAPS), toxoplasmosis-transplant, organ transplant, tissue transplant, traumatic brain injury, tuberculosis, type 1 diabetes, type 2 diabetes, uveitis.

In some embodiments, the disease is chosen from acute lymphocytic leukemia, Addison's disease, adrenal hyperplasia, adrenocortical insufficiency, allergic conjunctivitis, alopecia, amyloidosis, angioedema, anterior segment inflammation, autoimmune hepatitis, Behcet's syndrome, berylliosis, bone pain, bursitis, carpal tunnel syndrome, chorioretinitis, chronic lymphocytic leukemia, corneal ulcer, diffuse intrinsic pontine glioma, epicondylitis, erythroblastopenia, gout, gouty arthritis, graft-versus-host disease, hemolytic anemia, Hodgkin's disease, hypercalcemia, hyperammonemia, hypoplastic anemia, idiopathic thrombocytopenic purpura, iritis, juvenile rheumatoid arthritis, keratitis, kidney transplant rejection prophylaxis, Loeffler's syndrome, mixed connective tissue disease, myasthenia gravis, mycosis fungiodes, optic neuritis, pemphigus, pneumonia, pneumonitis, polychondritis, psoriasis, rheumatic carditis, severe pain, sickle cell, sickle cell anemia, Stevens-Johnson syndrome, temporal arteritis, tenosynovitis, thyroiditis, urticarial, Wegener's granulomatosis, and weight loss.

In some embodiments, the disease is asthma or chronic obstructive pulmonary disease In some embodiments, the disease is Sjogren's syndrome.

In some embodiments, the disease is arthritis.

In some embodiments, the disease is muscular wasting.

In some embodiments, the muscular wasting disease is muscular dystrophy.

In some embodiments, the muscular dystrophy is chosen from Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the muscular dystrophy is Duchenne muscular dystrophy.

In certain embodiments, vamorolone Form I is administered at a dose of from 0.1 to 500 mg/kg per day. The dose range for adult humans is generally from 5 mg to 2 g/day. In some embodiments, the dose range is 0.25 to 6.0 mg/kg/day, such as 0.25 mg/kg/day, 0.75 mg/kg/day, 2.0 mg/kg/day, or 6.0 mg/kg/day.

For example, provided herein are the following embodiments.

Embodiment 1

An aqueous oral pharmaceutical suspension composition comprising:
vamorolone Form I;
at least one suspending agent; and
at least one suspension vehicle.

Embodiment 2

The suspension of Embodiment 1, comprising vamorolone Form I in an amount of between about 2% and about 10% w/w.

Embodiment 3

The suspension of Embodiment 2, comprising vamorolone Form I in an amount of about 4% w/w.

Embodiment 4

The suspension of any of the preceding Embodiments, wherein the suspending agent is chosen from acacia, agar, alginic acid or a salt thereof, bentonite, carbomers, carboxymethylcellulose or a salt thereof, carrageenan, corn starch, ethylcellulose, gelatin, guar gum, hydroxyethylcellulose, hydroxyethylmethylcellulose, hydroxypropylcellulose, hydroxypropylmethylcellulose, methylcellulose, microcrystalline cellulose, pectin, polyvinyl alcohol, polyvinyl pyrrolidone, polyethylene oxide, colloidal silicon dioxide, tragacanth, xanthan gum, and mixtures thereof (and including salts of any of the foregoing).

Embodiment 5

The suspension of Embodiment 4, wherein the suspending agent is chosen from carboxymethylcellulose or a salt thereof, microcrystalline cellulose, xanthan gum, and mixtures thereof.

Embodiment 6

The suspension of Embodiment 4, wherein the suspending agent comprises a mixture of microcrystalline cellulose, xanthan gum, and carboxymethylcellulose, or a salt thereof.

Embodiment 7

The suspension of Embodiment 4, wherein the suspending agent comprises a mixture of microcrystalline cellulose, xanthan gum, and sodium carboxymethylcellulose.

Embodiment 8

The suspension of any of the preceding Embodiments, wherein the at least one suspending agent is present in an amount of between about 0.5% to about 5% w/w.

Embodiment 9

The suspension of any of the preceding Embodiments, wherein the suspension vehicle is chosen from xylitol, propylene glycol, glycerin, sorbitol, liquid glucose, dextrose, and mixtures thereof.

Embodiment 10

The suspension of Embodiment 9, wherein the suspension vehicle is propylene glycol, dextrose, or a mixture thereof.

Embodiment 11

The suspension of any one of the preceding Embodiments, wherein the suspension vehicle is present in an amount of from about 3% to about 10% w/w.

Embodiment 12

The suspension of claim 11, wherein the suspension vehicle comprises glycerin, the suspension agent comprises xanthan gum, and vamorolone Form I in an amount of about 4% w/w.

Embodiment 13

The suspension of any of the preceding Embodiments, wherein vamorolone Form I is further characterized by an X-ray powder diffraction pattern comprising peaks, in terms of °2θ, at about 11.9, about 13.7, about 16.1, and about 18.3 with radiation Cu Kα.

Embodiment 14

The suspension of any of the preceding Embodiments, wherein vamorolone Form I is further characterized by an X-ray powder diffraction pattern substantially as shown in FIG. 1.

Embodiment 15

The suspension of any of the preceding Embodiments, wherein vamorolone Form I is further characterized by an exothermic event onset at 180.7° C. and a melting event with an onset and peak temperatures of 231.0° C. and 234.7° C., respectively, as measured by differential scanning calorimetry.

Embodiment 16

The suspension of Embodiment 15, wherein vamorolone Form I is further characterized by a differential scanning calorimetry trace substantially as shown in FIG. 3.

Embodiment 17

The suspension of any of the preceding Embodiments, wherein vamorolone Form I is further characterized by a thermogravimetric analysis profile showing less than about 0.5% weight loss below about 175° C.

Embodiment 18

The suspension of Embodiment 17, wherein vamorolone Form I is further characterized by a thermogravimetric analysis profile substantially as shown in FIG. 2.

Embodiment 19

The suspension of any one of the preceding Embodiments, wherein the vamorolone Form I has a chemical purity of at least about 95%, at least about 96%, at least about 97%, at least about 98%, at least about 99%, or at least about 99.5% by high performance liquid chromatography.

Embodiment 20

The suspension of any one of the preceding Embodiments, wherein the suspension has total chemical impurities of not more than about 0.6% by high performance liquid chromatography.

Embodiment 21

The suspension of any one of the preceding Embodiments, wherein the suspension has not more than about 0.5% by high performance liquid chromatography of an epoxide having the formula:

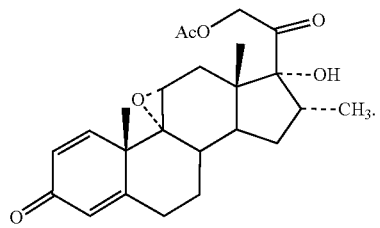

Embodiment 22

A method of treating or reducing the symptoms of muscular dystrophy, comprising the administration, to a patient in need thereof, of a therapeutically effective amount of a suspension of any one of Embodiments 1 to 20.

Embodiment 23

The method of Embodiment 22, wherein the therapeutically effective amount is between 10 mg to 200 mg.

Embodiment 24

The method of Embodiment 22, wherein the therapeutically effective amount is between 0.01 mg/kg to 10.0 mg/kg.

Embodiment 25

The method of Embodiment 22, wherein the therapeutically effective amount is between 2 mg/kg to 6.0 mg/kg.

Embodiment 26

The method of any one of Embodiments 22 to 25, wherein the muscular dystrophy is chosen from Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

All references, patents or applications, U.S. or foreign, cited in the application are hereby incorporated by reference as if written herein in their entireties. Where any inconsistencies arise, material literally disclosed herein controls.

Further embodiments include the embodiments disclosed in the following Examples, which is not to be construed as limiting in any way.

EXAMPLES

The following examples are included to demonstrate some embodiments of the disclosure. It should be appreciated by those of skill in the art that the techniques disclosed in the examples represent techniques discovered by the inventors to function well in the practice of the disclosure. Those of skill in the art should, however, in light of the present disclosure, appreciate that many changes can be made in the specific embodiments that are disclosed and still obtain a like or similar result without departing from the spirit and scope of the disclosure, therefore all matter set forth is to be interpreted as illustrative and not in a limiting sense.

Example 1

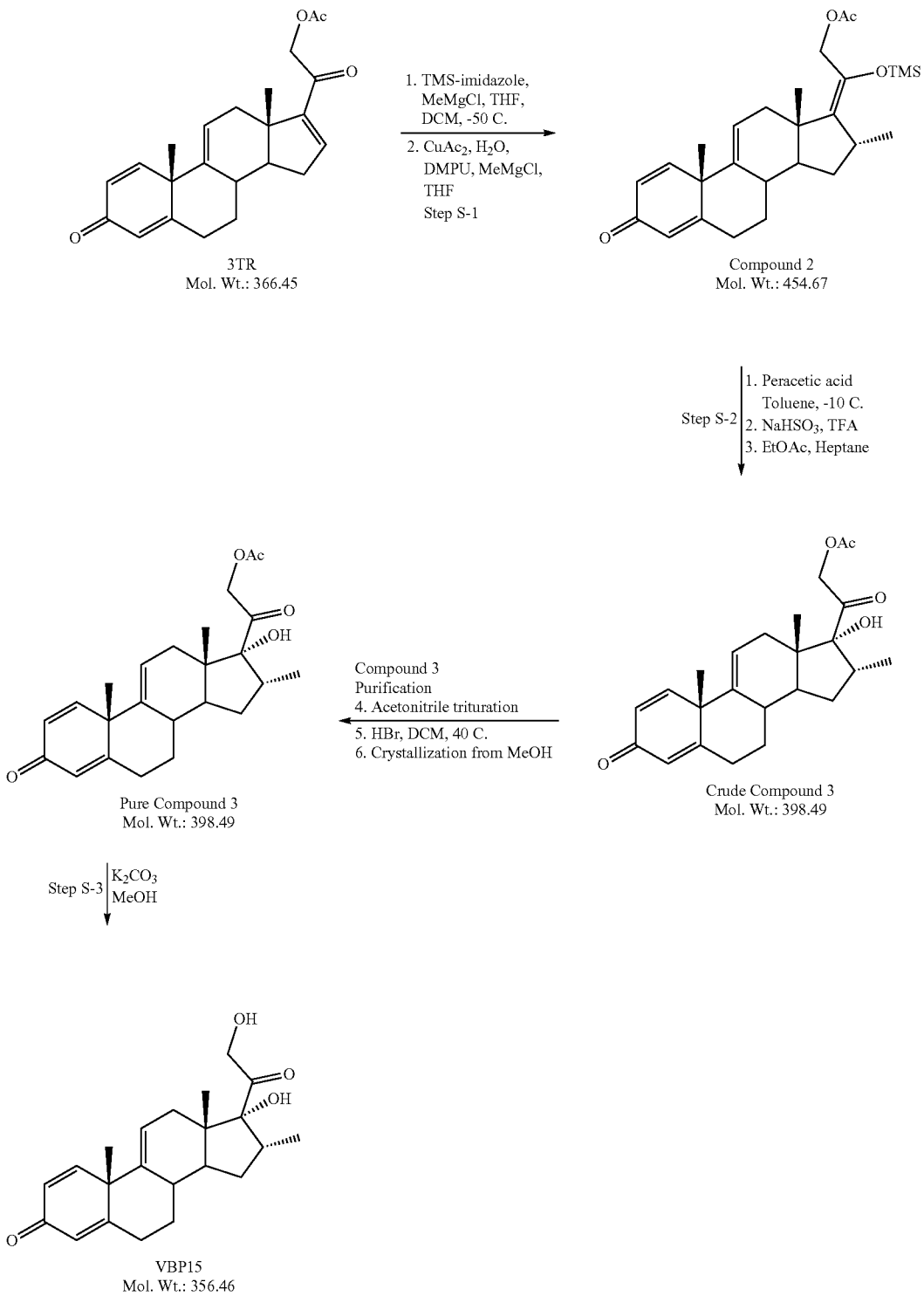

Compound 2 Preparation

3-TR (100 g, 273 mmol), dichloromethane (DCM, 500 mL) and tetrahydrofuran (THF, 400 mL) were charged to a reaction flask under nitrogen. To this was charged trimethylsilyl imidazole (TMS-imidazole, 65.3 g, 466 mmol, 1.7 eq). The resulting mixture was stirred at room temperature for 3 hours.

In a separate flask, copper acetate monohydrate (5.4 g, 27 mmol), tetrahydrofuran (400 ml) and 1,3-dimethyl-3,4,5,6-tetrahydro-2(1H)-pyrimidinone (DMPU, 53.3 g, 416 mmol) were combined and stirred at room temperature for approximately 3 hours. The blue mixture was subsequently cooled to −50° C., and to this was added methyl magnesium chloride solution (27 ml, 3.0 M in THF, 82 mmol) dropwise. After 30 minutes, the mixture had formed a deep blue, sticky "ball."

The 3-TR/TMS-imidazole mixture was cooled to −50° C. and to this was charged the copper acetate/DMPU solution above via canula. The residual sticky mass from the copper acetate/DMPU mixture was dissolved using DCM (50 mL) and also transferred.

Methyl magnesium chloride (123.2 mL, 3.0 M solution in THF, 368 mmol) was added dropwise over 45 minutes to the combined reaction mixtures, which were then allowed to stir for 2 hours at −50° C. Subsequent HPLC analysis showed complete consumption of starting material. The mixture was allowed to warm to room temperature overnight, with stirring.

Toluene (800 mL) was added to the mixture, followed by 5% acetic acid solution (600 mL). The aqueous layer was removed and discarded. The acetic acid wash was repeated. The organic layer was washed with brine (400 mL), 5% sodium bicarbonate solution (400 mL×2), followed by a brine wash (400 mL). The organic solution was dried over sodium sulfate, then concentrated to dryness under reduced pressure. The product was recovered as a viscous, light golden oil. Mass recovery was 146 grams (119% of theoretical).

Step 2 Compound 3 Preparation

Compound 2 (92 g, 202 mmol) and toluene (1000 mL, 10.9 vol) were charged to a reaction flask under nitrogen and the solution was cooled to −10° C. A 32 wt % solution of peracetic acid in acetic acid (60 mL, 283 mmol, 1.4 eq) was added dropwise over about 30 min maintaining the temperature at −10° C. The reaction was held for approximately 20 h (HPLC showed 75% Cmpd 3, Cmpd 2 1.5%, 6% diastereomer; 5% epoxide). Starting at −10° C., a 20% aqueous solution of sodium bisulfite (920 mL, 10 vol) was added carefully via addition funnel, keeping the temperature below 10° C. Trifluoroacetic acid (16 mL, 202 mmol, 1 eq) was added and the mixture was held for 3 h at 0-5° C. to complete desilylation (endpoint by HPLC). The lower aqueous layer was drained, and the organic layer was washed with a saturated solution of sodium bicarbonate (3×250 mL), followed by water (1×250 mL), and brine (1×150 mL). The organic layer was then dried over $Na_2SO_4$, filtered and concentrated to a pasty solid (89 g). The residue was taken up in 1.5 vol of EtOAc and transferred to neat heptane (19 vol) to precipitate crude Cmpd 3 as an off-white solid (50 g, 62.5% yield; HPLC 79% Cmpd 3, 5.6% epoxide, 1.7% diastereomer). The crude Cmpd 3 (48.5 g) was triturated in hot acetonitrile (2 vol) at 60° C. for 4 h, and then gradually cooled to ambient temperature overnight. The mixture was filtered using the recycled filtrate to rinse and wash the wet cake. After drying, the recovery was 64.3% (31.2 g; HPLC 93.5% Cmpd 3, 3.3% epoxide). To remove the epoxide impurity, the 31 Cmpd 3 was dissolved in DCM (250 mL, 8 vol) and a solution of 48% HBr in water was added (7.5 mL). The mixture was heated at 40° C. for 1 h (HPLC<0.3% epoxide). The mixture was cooled and transferred to a separatory funnel. The lower aqueous layer (brown) was removed and the upper organic layer was washed with water (200 mL), saturated $NaHCO_3$ (150 mL), and brine (100 mL). The organic layer was dried over $Na_2SO_4$, filtered, and concentrated to a tan foam (32 g, ~100% recovery). Methanol (64 mL, 2 vol) was added to the 32 g foam forming a slurry. To this was added a 1:1 solution of MeOH:water (60 mL, 2 vol) dropwise. The slurry cooled to slightly below ambient temperature and filtered using recycled filtrate to rinse and wash the wet cake. The solids were dried to constant weight, affording 26.1 g Cmpd 3 (81% recovery; HPLC 97.8%). The overall yield for Step 2 was 32.5%.

Step 3 VBP15 Preparation

Compound 3 (26 g, 65 mmol) and MeOH (156 mL, 6 vol) were mixed in a reaction flask and cooled to 0-5° C. A solution of $K_2CO_3$ (9.9 g, 72 mmol, 1.1 eq) in water (65 mL) was added dropwise, and the mixture was allowed to gradually warm to ambient temperature overnight. Analysis by HPLC showed 2.5% SM and another 5 mol % $K_2CO_3$ was added and the mixture stirred for another day (HPLC endpoint 1.1% Cmpd 3). The mixture was neutralized to pH 7 with 1.5 M HCl (53 mL) and ~25% of the MeOH (30 g) was removed under vacuum to maximize recovery. After stirring for 2 days, the product was isolated by filtration using the recycled filtrate to aid transferring the wet cake to the funnel. The wet cake was dried under vacuum, affording 19.3 g VBP15 (83% yield) as an off-white powder. Analysis of the solids by HPLC showed 98.8% purity with 0.6% Cmpd 3 as the only major impurity.

Example 2—Preparation of Vamorolone Form I

Power X-Ray Diffraction (pXRD)

The solid samples were examined using X-ray diffractometer (Bruker D8 advance). The system is equipped with highly-parallel x-ray beams (Gobel Mirror) and LynxEye detector. The samples were scanned from 3 to 40°2θ, at a step size 0.02°2θ and a time per step of 19.70 seconds. The tube voltage and current were 45 kV and 40 mA, respectively. The sample was transferred from sample container onto zero background XRD-holder and gently ground.

TGA Analysis

TGA analyses were carried out on a TA Instruments TGA Q500. Approximately 2.0 mg of samples was placed in a tared platinum or aluminum pan, automatically weighed, and inserted into the TGA furnace. The samples were heated at a rate of 10° C./min, to final temperature of 300° C. The purge gas is nitrogen for balance at 40 ml/min and for the sample at 60 mL/min, respectively.

DSC Analysis

DSC analyses were conducted on a TA Instruments Q200. The calibration standard was indium. A sample 2.0 mg in weight was placed into a TA DSC pan, and weight accurately recorded. Crimped pans were used for analysis and the samples were heated under nitrogen (50 ml/min) at a rate of 10° C./min, up to a final temperature of 260° C.

Preparation of Drug Solutions

Drug substance was weighted into glass vials, the vials were then each filled with about 5 mL of the desired solvents, stirred (vortex mixer) and heated to 45° C. Residue suspensions consisting of primarily solid particulates were later used for slurry studies.

Filtration of Drug Solutions/Suspensions

All drug solutions/suspensions were manually filtered into clean glass vials using plastic non-contaminating syringes equipped with 0.22-μm nylon filter cartridges. The filtrates were then used for crystallization/precipitation studies as outlined below.

Well Plate Preparation/Solvent Distribution/Crystallization

The saturated drug solutions (filtrates) were distributed in a 96-well plate. The solvents in plate were allowed to evaporate in an operating laboratory fume hood under ambient conditions of temperature and humidity. The plate was covered for the slow solvent evaporation (crystallization) condition. During the process of crystallization, the plate was visually examined and any solid material was analyzed by imaging system, powder x-ray diffraction (PXRD), differential scanning calorimetry (DSC), and thermogravimetric analysis (TGA), as deemed appropriate based on amount of sample.

The table below lists the solvent(s) from which vamorolone Form I was crystallized following the parameters in Table 1.

TABLE 1

| Solvent 1 | Solvent 2 |
|---|---|
| Acetonitrile | Acetonitrile |
| Acetonitrile | Methanol |
| Acetonitrile | THF |
| Acetonitrile | Heptane |
| Acetonitrile | Water |
| Acetonitrile | Nitromethane |
| Acetone | Ethyl acetate |
| Acetone | Methanol |
| Acetone | THF |
| Acetone | Toluene |
| Acetone | 2-Butanone |
| Acetone | Heptane |
| Acetone | Water |
| Acetone | Nitromethane |
| ethanol | ethanol |
| ethanol | Methanol |
| Ethyl acetate | Toluene |
| Ethyl acetate | Heptane |
| Ethyl acetate | Nitromethane |
| Methanol | Methanol |
| Methanol | 2-propanol |
| Methanol | THF |
| Methanol | Toluene |
| Methanol | 2-Butanone |
| Methanol | dichloromethane |
| Methanol | Water |
| Methanol | Nitromethane |
| THF | THF |
| THF | 2-Butanone |
| THF | Heptane |
| THF | Nitromethane |
| Toluene | 2-Butanone |
| Toluene | dichloromethane |
| Toluene | Nitromethane |
| 2-Butanone | 2-Butanone |
| 2-Butanone | Heptane |
| dichloromethane | Heptane |
| Heptane | Nitromethane |
| Nitromethane | Nitromethane |

The crystallized compound was characterized by pXRD (FIG. 1), TGA (FIG. 2), and DSC (FIG. 3), which is assigned as Form I. TGA profile showed that little weight loss was observed prior to decomposition. DSC profile showed that there is exothermic event, which suggested that phase transformation/re-crystallization occurred with onset temperature 180.7° C. Then, the crystal solid melted with onset and peak temperatures of 231.0 and 234.7° C., respectively, and enthalpy 88.5 J/g.

The drug compound was thermally treated using DSC cell at various heating rate at 2.0, 5.0, 10.0, 20.0, and 40° C. per minute. The results further confirmed that recrystallization or phase transformation has occurred during the heating process.

A sample, isolated by heating the drug substance in DSC pan to 206° C. and rapidly cooled down, was examined by pXRD, and its pXRD pattern is similar to the original sample.

Figure 4:
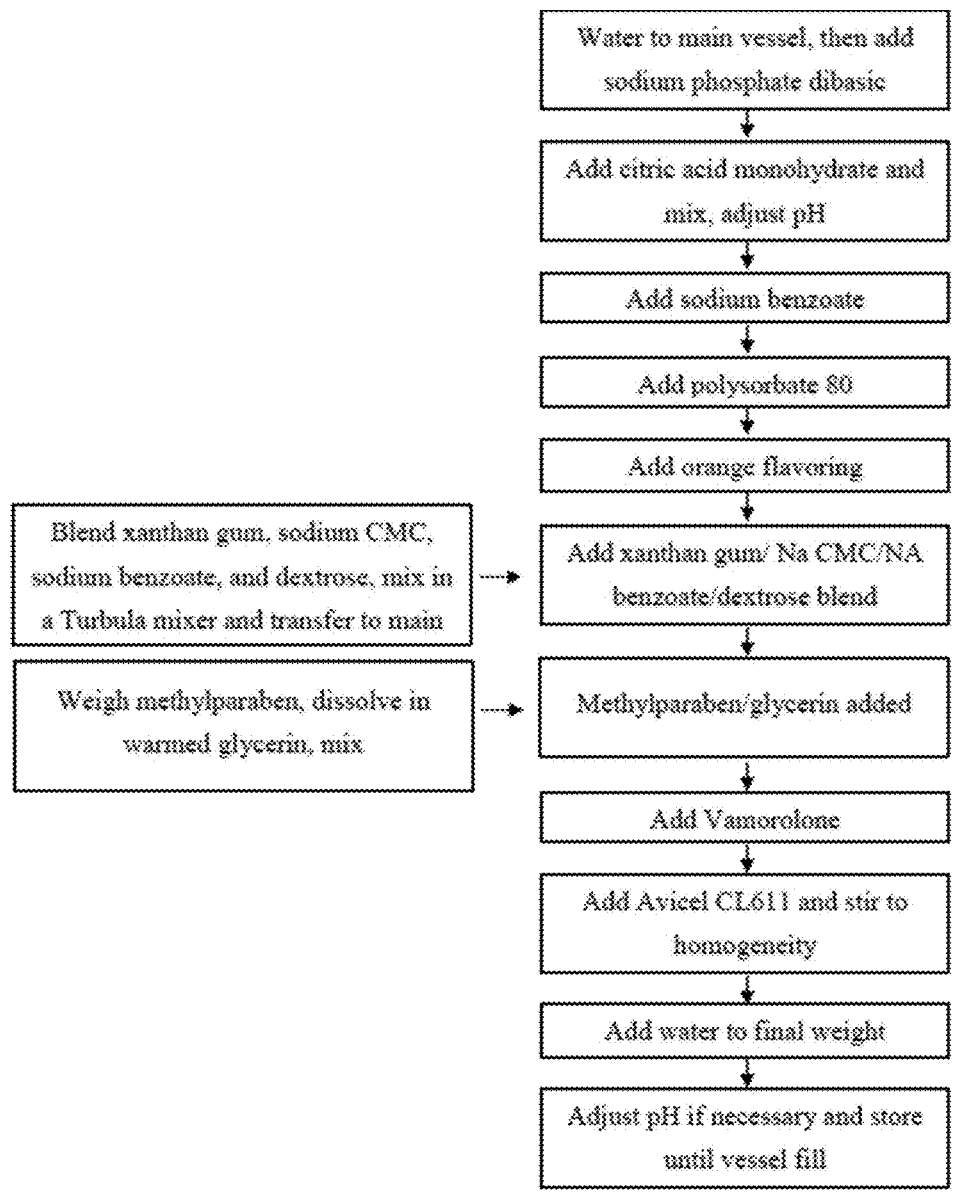
FIG. 4 shows a flow diagram for the manufacturing process used to make the aqueous oral pharmaceutical suspension composition comprising vamorolone Form I described in Example 3.

Example 3—Preparation of an Aqueous Oral Pharmaceutical Suspension Composition Comprising Vamorolone Form I An oral pharmaceutical composition was prepared as a suspension by blending the ingredients in the amounts listed below at Table 2 to form a suspension. FIG. 4 shows a flow diagram for the manufacturing process used to prepare this suspension.

TABLE 2

| Ingredient | Amount (grams) |
|---|---|
| Vamorolone | 4.0 |
| Sodium Carboxymethylcellulose, Medium Viscosity, USP | 0.5 |
| Xanthan Gum, NF | 0.15 |
| Dextrose Anhydrous, USP | 1.0 |
| Polysorbate 80, NF | 0.1 |
| Avicel CL611 Microcrystalline cellulose, NF | 2.2 |
| Sodium Phosphate Dibasic, Anhydrous USP Grade | 0.19 |
| Citric Acid Monohydrate, Granular USP | 0.19 |
| Methylparaben, Ph. Eur./NF | 0.1 |
| Sodium Benzoate NF | 0.1 |
| Glycerin, USP | 5.0 |
| Orange flavor 58.4108.UL PHA | 0.1 |
| Sterile Purified Water, USP | Qs to 100 |

* "Qs" denotes the volume of sterile water necessary to bring the composition to 100 wt. %.

Figure 5:
FIG. 5 shows a flow diagram for the manufacturing process used to make the aqueous oral pharmaceutical suspension composition comprising vamorolone Form I described in Example 4.

Example 4—Preparation of an Aqueous Oral Pharmaceutical Suspension Composition Comprising Vamorolone Form I An oral pharmaceutical composition was prepared as a suspension by blending the ingredients in the amounts listed below at Table 3 to form a suspension. FIG. 5 shows a flow diagram for the manufacturing process used to prepare this suspension.

TABLE 3

| Ingredient | Amount (grams) |
|---|---|
| Vamorolone | 4.0 |
| Sodium Carboxymethyl cellulose, Medium Viscosity, USP | 0.5 |
| Xanthan Gum, NF | 0.15 |
| Dextrose Anhydrous, USP | 1.0 |
| Polysorbate 80, NF | 0.1 |
| Avicel CL611 Microcrystalline cellulose, NF | 0.6 |
| Sodium Phosphate Dibasic, Anhydrous USP Grade | 0.19 |
| Citric Acid Monohydrate, Granular USP | 0.19 |
| Methylparaben, Ph.Eur./NF | 0.1 |
| Sodium Benzoate NF | 0.1 |
| Propylene Glycol, USP | 5.0 |
| Orange flavor 58.4108.UL PHA | 0.1 |
| Sterile Purified Water, USP | Qs to 100 |

Example 5—Stability Data

Stability results for Vamorolone (Orange) Suspension stored at 5° C. and 25° C./60% relative humidity are provided below at Tables 4-6. A HPLC method as shown in the table below was used to identify and assay the impurities.

TABLE 4

| Column | SiliaChrom ™ dt $C_{18}$ (150 × 4.6 mm, 3.0 μm)* |
|---|---|
| Mobile Phase A | Water |
| Mobile Phase B | Acetonitrile |

| Gradient elution | Time (min.) | % Mobile Phase B |
|---|---|---|
| | 0 | 25 |
| | 15 | 40 |
| | 22 | 100 |
| | 27 | 100 |

TABLE 4-continued

| | 32 | 25 |
|---|---|---|
| Flow rate | 1.5 mL/min | |
| Column Temperature | 45° C. ± 2° C. | |
| Injection Volume | 10 μL | |
| Needle and Column Wash | 50/50 (v/v) $H_2$/Acetonitrile | |
| Detection | UV 240 nm (reference wavelength 390 nm as needed) | |
| Run Time | 32 minutes | |

SiliaChrom® dt $C_{18}$ is a reverse-phase $C_{18}$ silica gel medium partially endcapped with trimethylsilyl groups and polar surface groups (diol), having a purity of the spherical silica gel is at 99.999%. This phase has no measurable metal content to avoid secondary interactions with basic or ion species.

TABLE 5

Stability results for orange formulation 40 mg/mL suspension long-term conditions (5° C.)

| Test Lot-044 | | Stability Interval (Months) | | | | | | | |
|---|---|---|---|---|---|---|---|---|---|
| Formulation of Example 4 | | Initial | 1 | 3 | 6 | 9 | 12 | 18 | 24 |
| Assay (% label claim) | | 101.2 | 99.5 | 100.2 | 100.8 | 98.4 | 100.8 | 102.0 | 99.9 |
| Individual Impurities (%) | RRT 1.05 | 0.08 | 0.09 | 0.09 | 0.09 | 0.09 | 0.09 | 0.09 | 0.09 |
| | RRT 1.38-1.40 | 0.27 | 0.27 | 0.28 | 0.27 | 0.27 | 0.27 | 0.28 | 0.27 |
| Total Impurities (%) | | 0.35 | 0.36 | 0.37 | 0.36 | 0.36 | 0.36 | 0.37 | 0.36 |
| pH (direct) | | 5.0 | 4.8 | 5.0 | 4.9 | 4.9 | 5.0 | 5.0 | 5.00 |

| Test Lot-143 | | Stability Interval (Months) | | | | | |
|---|---|---|---|---|---|---|---|
| Formulation of Example 3 | | Initial | 1 | 3 | 6 | 9 | 12 |
| Assay (% label claim) | | 98.2 | 98.1 | 99.4 | 99.4 | 100.1 | 99.6 |
| Individual Impurities (%) | RRT 1.05 | 0.16 | 0.16 | 0.15 | 0.16 | 0.15 | 0.16 |
| | RRT 1.27-1.28 | 0.14 | 0.13 | 0.13 | 0.14 | 0.14 | 0.13 |
| | RRT 1.38-1.40 | 0.25 | 0.25 | 0.25 | 0.25 | 0.24 | 0.24 |
| Total Impurities (%) | | 0.55 | 0.54 | 0.53 | 0.55 | 0.53 | 0.53 |
| pH (direct) | | 5.0 | 5.0 | 5.0 | 4.9 | 5.0 | 5.0 |
| Viscosity (cP) | | >499.9 | NT | >499.9 | >499.9 | NT | >499.9 |

| Test Lot-155 | | Stability Interval (Months) | | | | | |
|---|---|---|---|---|---|---|---|
| Formulation of Example 3 | | Initial | 1 | 3 | 6 | 9 | 12 |
| Assay (% label claim) | | 99.2 | 100.4 | 99.7 | 97.9 | 100.2 | 99.9 |
| Individual Impurities (%) | RRT 1.05 | 0.16 | 0.16 | 0.16 | 0.15 | 0.15 | 0.14 |
| | RRT 1.27-1.28 | 0.13 | 0.14 | 0.13 | 0.13 | 0.13 | 0.14 |
| | RRT 1.38-1.40 | 0.24 | 0.25 | 0.24 | 0.24 | 0.24 | 0.25 |
| Total Impurities (%) | | 0.53 | 0.55 | 0.53 | 0.52 | 0.52 | 0.53 |
| pH (direct) | | 5.0 | 5.0 | 4.9 | 5.0 | 5.0 | 5.0 |
| Viscosity (cP) | | >499.9 | NT | >499.9 | >499.9 | NT | >499.9 |

| Test Lot-142 | | Stability Interval (Months) | | | | | |
|---|---|---|---|---|---|---|---|
| Formulation of Example 3 | | Initial | 1 | 3 | 6 | 9 | 12 |
| Assay (% label claim) | | 99.5 | 99.8 | 100.0 | 98.8 | 99.3 | 98.5 |
| Individual Impurities (%) | RRT 1.05 | 0.15 | 0.15 | 0.15 | 0.16 | 0.16 | 0.15 |
| | RRT 1.27-1.28 | 0.14 | 0.13 | 0.13 | 0.14 | 0.13 | 0.12 |
| | RRT 1.38-1.40 | 0.25 | 0.25 | 0.25 | 0.25 | 0.24 | 0.23 |
| Total Impurities (%) | | 0.54 | 0.53 | 0.53 | 0.55 | 0.53 | 0.50 |
| pH (direct) | | 5.0 | 5.0 | 5.0 | 5.0 | 5.0 | 5.0 |
| Viscosity (cP) | | 489.4 | NT | >499.9 | >499.9 | NT | >499.9 |

TABLE 6

Stability results for orange formulation 40 mg/mL suspension long-term conditions (25° C./60% RH)

Test Lot-044

| Formulation of Example 4 | | Initial | 1 | 3 | 6 | 12 |
|---|---|---|---|---|---|---|
| Assay (% label claim) | | 101.2 | 102.0 | 102.8 | 102.8 | 102.3 |
| Individual Impurities (%) | RRT 1.05 | 0.08 | 0.09 | 0.09 | 0.09 | 0.09 |
| | RRT 1.38-1.40 | 0.27 | 0.27 | 0.28 | 0.27 | 0.27 |
| Total Impurities (%) | | 0.35 | 0.36 | 0.37 | 0.36 | 0.36 |
| pH (direct) | | 5.0 | 4.9 | 5.0 | 4.9 | 5.0 |

Test Lot-143

| Formulation of Example 3 | | Initial | 1 | 3 | 6 | 12 |
|---|---|---|---|---|---|---|
| Assay (% label claim) | | 98.2 | 99.3 | 99.6 | 99.7 | 100.3 |
| Individual Impurities (%) | RRT 1.05 | 0.16 | 0.16 | 0.16 | 0.16 | 0.16 |
| | RRT 1.27-1.28 | 0.14 | 0.13 | 0.14 | 0.14 | 0.13 |
| | RRT 1.38-1.40 | 0.25 | 0.25 | 0.25 | 0.24 | 0.24 |
| Total Impurities (%) | | 0.55 | 0.54 | 0.55 | 0.54 | 0.53 |
| pH (direct) | | 5.0 | 5.0 | 5.0 | 4.9 | 5.0 |
| Viscosity (cP) | | >499.9 | NT | >499.9 | >499.9 | >499.9 |

Test Lot-155

| Formulation of Example 3 | | Initial | 1 | 3 | 6 | 12 |
|---|---|---|---|---|---|---|
| Assay (% label claim) | | 99.2 | 100.2 | 99.5 | 99.7 | 101.2 |
| Individual Impurities (%) | RRT 1.05 | 0.16 | 0.16 | 0.16 | 0.15 | 0.14 |
| | RRT 1.27-1.28 | 0.13 | 0.13 | 0.13 | 0.13 | 0.14 |
| | RRT 1.38-1.40 | 0.24 | 0.25 | 0.24 | 0.24 | 0.25 |
| Total Impurities (%) | | 0.53 | 0.54 | 0.53 | 0.52 | 0.53 |
| pH (direct) | | 5.0 | 5.0 | 4.9 | 5.0 | 5.0 |
| Viscosity (cP) | | >499.9 | NT | >499.9 | >499.9 | >499.9 |

Test Lot-142

| Formulation of Example 3 | | Initial | 1 | 3 | 6 | 12 |
|---|---|---|---|---|---|---|
| Assay (% label claim) | | 99.5 | 99.4 | 99.7 | 105.7 | 99.4 |
| Individual Impurities (%) | RRT 1.05 | 0.15 | 0.15 | 0.14 | 0.16 | 0.15 |
| | RRT 1.27-1.28 | 0.14 | 0.13 | 0.13 | 0.13 | 0.13 |
| | RRT 1.38-1.40 | 0.25 | 0.25 | 0.25 | 0.26 | 0.23 |
| Total Impurities (%) | | 0.54 | 0.53 | 0.52 | 0.55 | 0.51 |
| pH (direct) | | 5.0 | 4.9 | 5.0 | 4.9 | 5.0 |
| Viscosity (cP) | | 489.4 | NT | >499.9 | >499.9 | >499.9 |

Example 6—Further Aqueous Oral Pharmaceutical Suspension Composition Comprising Vamorolone Oral pharmaceutical compositions were prepared as a suspension by blending the ingredients in the amounts listed below at Table 7 to form a suspension.

TABLE 7

| | 4% Vamorolone formulations (wt. %) | | | |
|---|---|---|---|---|
| Ingredient | 1.3 | 2.2 | 2.3 | 3.1 |
| Vamorolone | 4.0 | 4.0 | 4.0 | — |
| Dextrose Anhydrous, USP | 1.0 | — | — | 1.0 |
| Sucralose | — | 0.1 | 0.1 | — |
| Sodium Carboxymethyl cellulose | 0.045 (high visc.) | — | — | 0.50 |
| Xanthan Gum, NF | — | 0.3 | 0.3 | 0.15 |
| Avicel CL591 Microcrystalline cellulose | 1.2 | — | — | 1.2 |
| Sodium Phosphate Dibasic, anhydrous | 0.28 | 0.28 | 0.28 | 0.19 |
| Citric Acid Monohydrate | 0.21 | 0.21 | 0.21 | 0.19 |
| Methylparaben | — | — | — | 0.10 |
| Sodium Benzoate | 0.5 | 0.5 | 0.20-0.10 | 0.20 |
| Potassium sorbate | 0.2 | 0.2 | — | — |
| Sodium EDTA | 0.1 | 0.1 | — | — |
| Glycerin | 5.0 | 5.0 | 5.0 | 5.0 |
| Orange flavor 58.4108.UL PHA | 0.1 | 0.1 | 0.1 | 0.1 |
| Sterile Purified Water, USP | Qs to 100 | Qs to 100 | Qs to 100 | Qs to 100 |
| pH | 4.0 | 4.0 | 4.0 | 5.0 |
| Viscosity (cP) | 598 | 424 | — | — |

Other uses of the disclosed methods will become apparent to those in the art based upon, inter alia, a review of this patent document.

What is claimed is:

1. An aqueous oral pharmaceutical suspension composition comprising:
   vamorolone Form I;
   at least one suspending agent; and
   at least one suspension vehicle.

2. The suspension of claim 1, comprising vamorolone Form I in an amount of between about 2% and about 10% w/w.

3. The suspension of claim 2, comprising vamorolone Form I in an amount of about 4% w/w.

4. The suspension of claim 1, wherein the suspending agent is chosen from acacia, agar, alginic acid or a salt thereof, bentonite, carbomers, carboxymethylcellulose or a salt thereof, carrageenan, corn starch, ethylcellulose, gelatin, guar gum, hydroxyethylcellulose, hydroxyethylmethylcellulose, hydroxypropylcellulose, hydroxypropylmethylcellulose, methylcellulose, microcrystalline cellulose, pectin, polyvinyl alcohol, polyvinyl pyrrolidone, polyethylene oxide, colloidal silicon dioxide, tragacanth, xanthan gum, and mixtures thereof.

5. The suspension of claim 4, wherein the suspending agent is chosen from carboxymethylcellulose or a salt thereof, microcrystalline cellulose, xanthan gum, and mixtures thereof.

6. The suspension of claim 4, wherein the suspending agent comprises a mixture of microcrystalline cellulose, xanthan gum, and carboxymethylcellulose, or a salt thereof.

7. The suspension of claim 4, wherein the suspending agent comprises a mixture of microcrystalline cellulose, xanthan gum, and sodium carboxymethylcellulose.

8. The suspension of claim 1, wherein the at least one suspending agent is present in an amount of between about 0.5% to about 5% w/w.

9. The suspension of claim 1, wherein the suspension vehicle is chosen from xylitol, propylene glycol, glycerin, sorbitol, liquid glucose, dextrose, and mixtures thereof.

10. The suspension of claim 9, wherein the suspension vehicle is propylene glycol, dextrose, or a mixture thereof.

11. The suspension of claim 1, wherein the suspension vehicle is present in an amount of from about 3% to about 10% w/w.

12. The suspension of claim 11, wherein the suspension vehicle comprises glycerin, the suspension agent comprises xanthan gum, and vamorolone Form I in an amount of about 4% w/w.

13. The suspension of claim 1, wherein vamorolone Form I is further characterized by an X-ray powder diffraction pattern comprising peaks, in terms of ° 2θ, at about 11.9, about 13.7, about 16.1, and about 18.3 with radiation Cu Kα.

14. The suspension of claim 1, wherein vamorolone Form I is further characterized by an X-ray powder diffraction pattern substantially as shown in FIG. 1.

15. The suspension of claim 1, wherein vamorolone Form I is further characterized by an exothermic event onset at 180.7° C. and a melting event with an onset and peak temperatures of 231.0° C. and 234.7° C., respectively, as measured by differential scanning calorimetry.

16. The suspension of claim 15, wherein vamorolone Form I is further characterized by a differential scanning calorimetry trace substantially as shown in FIG. 3.

17. The suspension of claim 1, wherein vamorolone Form I is further characterized by a thermogravimetric analysis profile showing less than about 0.5% weight loss below about 175° C.

18. The suspension of claim 17, wherein vamorolone Form I is further characterized by a thermogravimetric analysis profile substantially as shown in FIG. 2.

19. The suspension of claim 1, wherein the vamorolone Form I has a chemical purity of at least about 95%, at least about 96%, at least about 97%, at least about 98%, at least about 99%, or at least about 99.5% by high performance liquid chromatography.

20. The suspension of claim 1, wherein the suspension has total chemical impurities of not more than about 0.6% by high performance liquid chromatography.

21. The suspension of claim 1, wherein the suspension has not more than about 0.5% by high performance liquid chromatography of an epoxide having the formula:

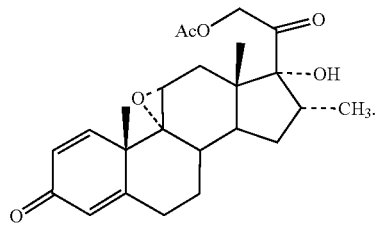

22. A crystalline form of vamorolone characterized by one or more of the following:
   (a) an X-ray powder diffraction pattern comprising two or more peaks, in terms of ° 2θ, at about 11.9, about 13.7, about 16.1, and about 18.3 with radiation Cu Kα;
   (b) an X-ray powder diffraction pattern substantially as shown in FIG. 1;
   (c) a thermogravimetric analysis profile showing less than about 0.5% weight loss below about 175° C.;
   (d) a thermogravimetric analysis profile substantially as shown in FIG. 2;
   (e) an exothermic event onset at 180.7° C. and a melting event with an onset and peak temperatures of 231.0° C. and 234.7° C., respectively, as measured by differential scanning calorimetry; and
   (f) a differential scanning calorimetry trace substantially as shown in FIG. 3, wherein the crystalline form has a chemical purity of at least about 95% by high throughput liquid chromatography.

23. The crystalline form of claim 22, having a chemical purity of at least about 96%, at least about 97%, at least about 98%, at least about 99%, or at least about 99.5% by high performance liquid chromatography.

24. A crystalline form of vamorolone characterized by one or more of the following:
   (g) an X-ray powder diffraction pattern comprising two or more peaks, in terms of ° 2θ, at about 11.9, about 13.7, about 16.1, and about 18.3 with radiation Cu Kα;
   (h) an X-ray powder diffraction pattern substantially as shown in FIG. 1;
   (i) a thermogravimetric analysis profile showing less than about 0.5% weight loss below about 175° C.;
   (j) a thermogravimetric analysis profile substantially as shown in FIG. 2;
   (k) an exothermic event onset at 180.7° C. and a melting event with an onset and peak temperatures of 231.0° C. and 234.7° C., respectively, as measured by differential scanning calorimetry; and
   (l) a differential scanning calorimetry trace substantially as shown in FIG. 3, wherein the crystalline form has a particle size such that d90 is less than about 50 μm.

25. An oral pharmaceutical composition comprising the crystalline form of vamorolone of claim 24.

26. An oral pharmaceutical composition comprising the crystalline form of vamorolone of claim 22.

* * * * *